(12) United States Patent
Jiang et al.

(10) Patent No.: US 12,145,152 B1
(45) Date of Patent: Nov. 19, 2024

(54) FLUID ANALYZING SYSTEM USING FILM-LEVER ACTUATED SWITCHES

(71) Applicants: ARIZONA BOARD OF REGENTS ON BEHALF OF ARIZONA STATE UNIVERSITY, Scottsdale, AZ (US); HANGZHOU VANTRONICS BIOTECHNOLOGY CO. LTD., Zhejiang (CN)

(72) Inventors: Hanging Jiang, Chandler, AZ (US); Chao Liang, Tempe, AZ (US); Senwei Xu, Zhejiang (CN)

(73) Assignees: ARIZONA BOARD OF REGENTS ON BEHALF OF ARIZONA, Scottsdale, AZ (US); HANGZHOU VANTRONICS BIOTECHNOLOGY CO. LTD., Zhejiang (CN)

( * ) Notice: Subject to any disclaimer, the term of this patent is extended or adjusted under 35 U.S.C. 154(b) by 0 days.

(21) Appl. No.: 18/690,486

(22) PCT Filed: Sep. 10, 2021

(86) PCT No.: PCT/CN2021/117693
§ 371 (c)(1),
(2) Date: Mar. 8, 2024

(87) PCT Pub. No.: WO2023/035224
PCT Pub. Date: Mar. 16, 2023

(51) Int. Cl.
*B01L 3/00* (2006.01)

(52) U.S. Cl.
CPC ... *B01L 3/502761* (2013.01); *B01L 2200/027* (2013.01); *B01L 2200/04* (2013.01);
(Continued)

(58) Field of Classification Search
None
See application file for complete search history.

(56) References Cited

U.S. PATENT DOCUMENTS

| 2010/0165784 A1* | 7/2010 | Jovanovich | F16K 99/0015 137/861 |
| 2010/0266432 A1* | 10/2010 | Pirk | F16K 99/0057 417/472 |

(Continued)

FOREIGN PATENT DOCUMENTS

| CN | 101750488 A | 6/2010 |
| CN | 102341691 A | 2/2012 |

(Continued)

OTHER PUBLICATIONS

International Search Report and Written Opinion for Application No. PCT/CN2021/117693 dated May 26, 2022 (7 pages).

*Primary Examiner* — Matthew D Krcha
*Assistant Examiner* — Brittany I Fisher
(74) *Attorney, Agent, or Firm* — Michael Best & Friedrich LLP

(57) ABSTRACT

A pneumatic-driven fluidic cartridge and systems and methods for operating the same. The cartridge includes a substrate layer, an actuator layer, and an elastic layer. A fluid channel formed in a surface of the substrate layer includes a first chamber and a second chamber separated by a block section. The actuator layer includes a lever positioned to extend across the block section. The elastic layer is positioned between the substrate layer and the actuator layer. The lever applies a force to the elastic layer restricts fluid flow from the first chamber to the second chamber and is configured to bend outwardly opening a channel between the block section and the elastic layer exceeds the first threshold pressure.

20 Claims, 21 Drawing Sheets

(52) U.S. Cl.
    CPC ... *B01L 2200/0668* (2013.01); *B01L 2200/16* (2013.01); *B01L 2300/087* (2013.01); *B01L 2400/043* (2013.01); *B01L 2400/0487* (2013.01); *B01L 2400/0633* (2013.01)

(56) References Cited

U.S. PATENT DOCUMENTS

| | | |
|---|---|---|
| 2011/0206576 A1 | 8/2011 | Woudenberg et al. |
| 2012/0177543 A1 | 7/2012 | Battrell et al. |
| 2014/0308688 A1 | 10/2014 | Grego et al. |

FOREIGN PATENT DOCUMENTS

| | | |
|---|---|---|
| CN | 102459565 A | 5/2012 |
| CN | 103648648 A | 3/2014 |

\* cited by examiner

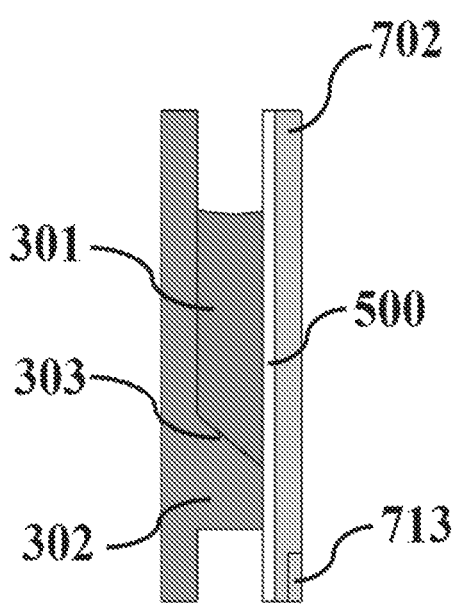
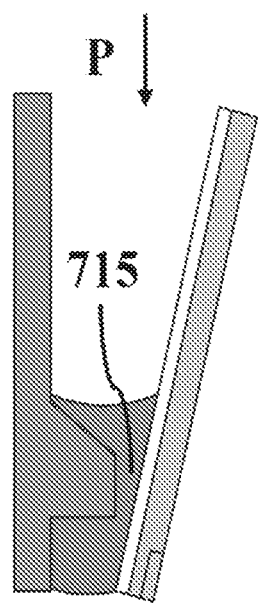
FIG. 10A
FIG. 10B
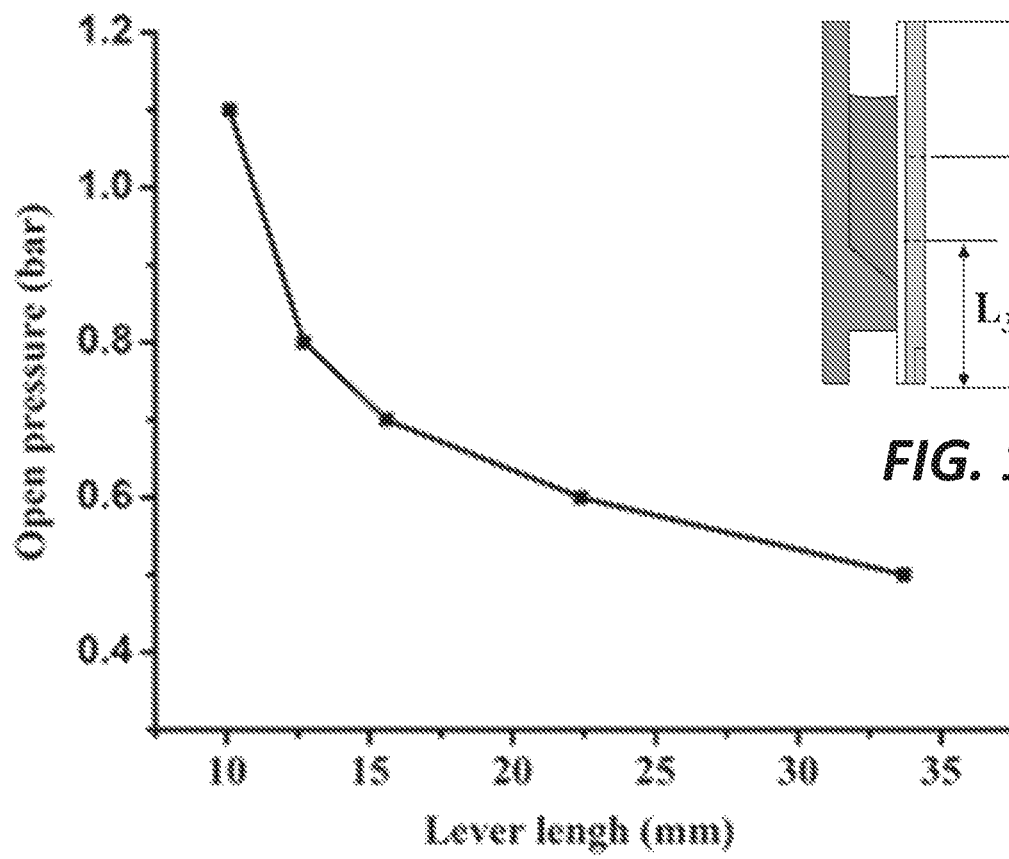
FIG. 11
FIG. 12

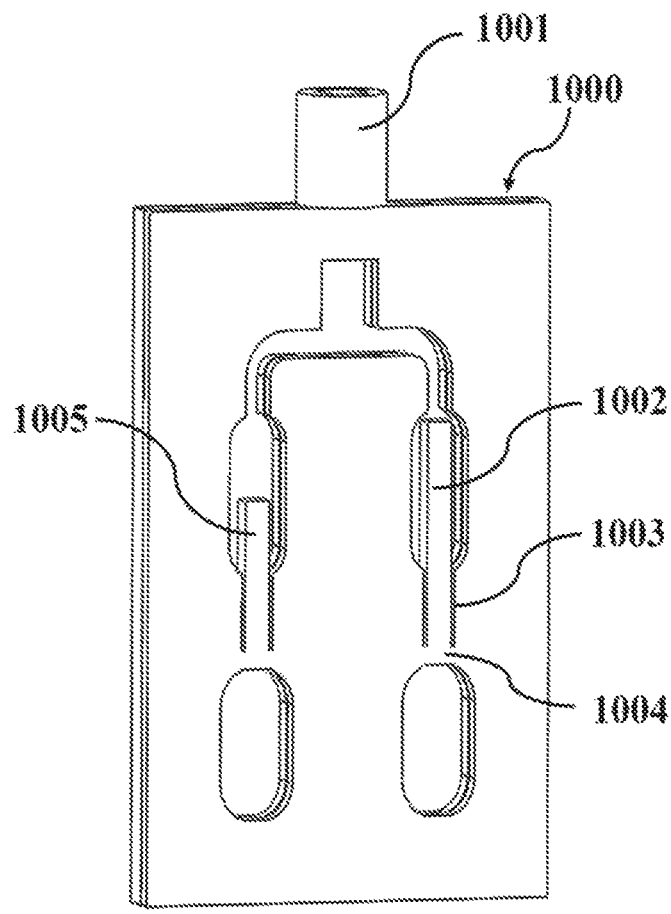
FIG. 15A
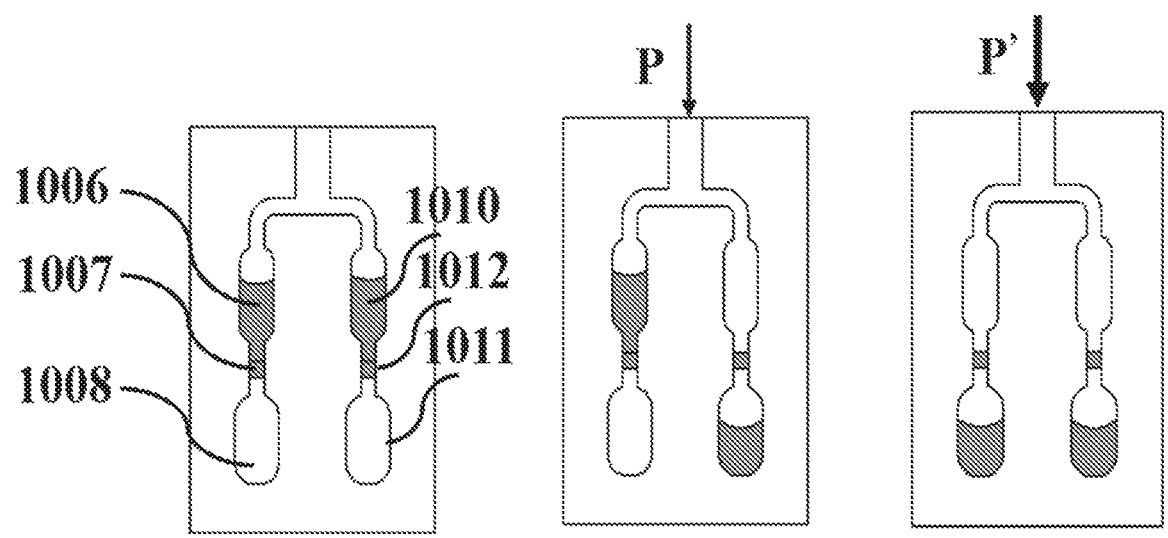
FIG. 15B  FIG. 15C  FIG. 15D

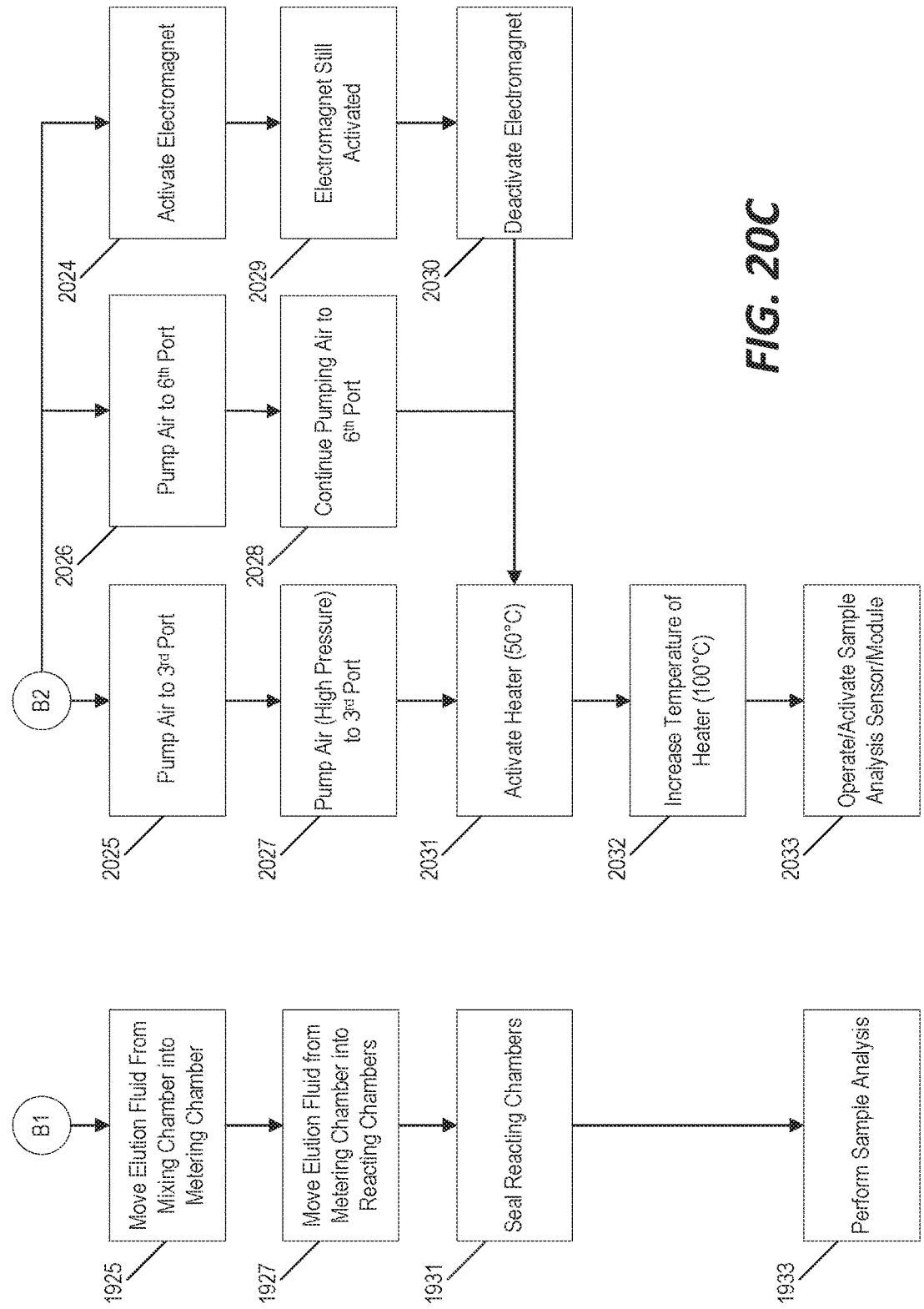

FLUID ANALYZING SYSTEM USING FILM-LEVER ACTUATED SWITCHES

BACKGROUND

This disclosure relates to systems and methods for fluid analysis. For example, some embodiments described herein relate to systems and methods for diagnostic fluid processing.

SUMMARY

Emerging human diseases are one of the major threats to global health and human civilization. Outbreaks like COVID-19 pandemic upend daily life and millions of people lost their life worldwide. Early, rapid, and accurate detection of diseases is important to controlling spread and for achieving better treatment outcomes. However, methods for detecting diseases in humans are often restricted to centralized laboratories. Patients and/or their samples are physically taken to a hospital or diagnostic clinic for testing and the testing results are often not available for several days. Moreover, for developing countries, disease detection is often delayed or ignored due to lack of skilled personnel and medical infrastructure.

Portable, easy-to-use, point-of-care testing (POCT) can address many of these concerns. Point-of-care testing devices are often based on the lateral flow principle (for example, a pregnancy test strip). In such devices, a reagent is pre-immobilized on the device in a dry state. Very small amounts of liquid sample are delivered by porous membrane to the reagents, dissolve the dried reagents, and produce a reaction that indicates a diagnostic result. However, this type of test strip cannot control the flow of the liquid sample precisely, cannot facilitate a controlled multistep reaction sequence, and cannot provide quantitative testing results. Another type of point-of-care testing device is a compact disc (CD)-like device that utilizes centrifugal force generated by a rotary motor to drive the liquid flow. Such devices can handle large amounts of sample and the testing process of such devices can be similar to the processes used in the centralized laboratories. Accordingly, these centrifugal-operated testing devices can have potential to achieve a more accurate quantitative testing results. However, such devices still have obvious limitations. For example, the centrifugal force is always outward, which means the liquid can only be transported to the outer rim of the device and more complicated testing processes cannot be conducted in such a device. Additionally, capillary valves are often used in such devices to control the flow state of the liquid. However, the capillary force can be dramatically affected by the channel geometry and surface properties of the device. Accordingly, any vibration or deviation of the surface property can cause unexpected liquid flow. Finally, the liquid flow in such device is continuous and cannot provide on-demand injection.

In various embodiments, the systems and methods described herein provide a biological analyzing system based on a film-lever actuated switch technology (FAST), which features a multidirectional, on-demand and robust testing process.

In one embodiment, the invention provides a pneumatic-driven fluidic cartridge comprising a substrate layer, an actuator layer, and an elastic layer. A fluid channel formed in a surface of the substrate layer includes a first chamber and a second chamber separated by a block section. The actuator layer includes a lever formed in the actuator layer and extending from the second chamber across the block section to the first chamber. The elastic layer is positioned between the substrate layer and the actuator layer. The lever of the actuator layer applies a sealing force to the elastic layer sufficient to prevent fluid flow from the first chamber to the second chamber when a pressure acting on the elastic layer from within the fluid channel is less than a first threshold pressure. The lever is configured to become bent outwardly by the pressure acting on the elastic layer from within the fluid channel when the pressure within the fluid channel exceeds the first threshold pressure. The outward bending of lever allows fluid to flow from the first chamber to the second chamber between the block section and the elastic layer.

In another embodiment, the invention provides a pneumatic-driven fluid cartridge system including an electronic controller, a pneumatic pump, and the pneumatic-driven fluidic cartridge.

In yet another embodiment, the invention provides a cartridge device for fluid sample analysis comprising a substrate layer, an elastic layer, an actuator layer, and a connector. The substrate layer includes a plurality of reagent chambers, a mixing chamber, a waste collection chamber and at least one reacting chamber all formed into a first surface of the substrate layer. The substrate layer also includes a plurality of block areas separating each reagent chamber from the mixing chamber, separating the mixing chamber from the waste collection chamber, and separating the mixing chamber from the at least one reacting chamber. The elastic layer is adhesively coupled to the first surface of the substrate layer, but is not adhesively coupled to the substrate layer at the block areas.

The actuator layer is separated from the substrate layer by the elastic layer and includes a plurality of displaceable reagent levers, a waste collection chamber lever, and a reacting chamber lever all formed in the actuator layer. Each reagent lever is positioned to extend across a different one of the block areas separating a reagent chamber from the mixing chamber and is configured to restrict fluid flow from the respective reagent chamber into the mixing chamber by applying a force to the elastic layer at the block area. Each reagent lever is also configured to bend outwardly away from the substrate layer in response to a sufficient pneumatic pressure applied to the reagent chamber. This outward bending allows fluid to flow from the reagent chamber into the mixing chamber. The waste collection lever is positioned to extend across the block area separating the mixing chamber from the waste collection chamber and is similarly configured to restrict fluid flow from the mixing chamber into the waste chamber by applying a second force to the elastic layer, but to bend outwardly when a first pneumatic pressure is applied to the mixing chamber. The reacting chamber lever is positioned to extend across the block area separating the mixing chamber from the reacting chamber and is configured to restrict fluid flow from the mixing chamber into the at least one reacting chamber, but to bend outwardly when a second pneumatic pressure is applied to the mixing chamber. The waste collection chamber lever is configured to bend outwardly in response to a lower pneumatic pressure in the mixing chamber than the second pneumatic pressure required to outwardly bend the reacting chamber lever.

The connector is coupled to the top edge of the cartridge and includes a plurality of openings each couplable to a pneumatic pump. The plurality of openings includes a mixing chamber opening coupled to the mixing chamber and a plurality of reagent chamber openings each coupled to a different one of the plurality of reagent chambers.

Other aspects of the invention will become apparent by consideration of the detailed description and accompanying drawings.

BRIEF DESCRIPTION OF THE DRAWINGS

FIG. 10A is a cross-sectional view of the pneumatic-pressure-activated film switch of FIG. 9A in a closed position.

FIG. 10B is a cross-sectional view of the pneumatic-pressure-activated film switch of FIG. 9A in an opened position.

FIG. 11 is a cross-sectional view of the pneumatic-pressure-activated film switch of FIG. 9A illustrating various different lever lengths.

FIG. 12 is a graph illustrating example of pressure levels required to open switches with different lever lengths.

FIG. 15A is a perspective view of a sequential injection film switch including a low pressure switch and a high pressure switch according to one embodiment.

FIG. 15B is an elevation view of an example of the sequential injection film switch of FIG. 15A before the low pressure switch or the high pressure switch are opened.

FIG. 15C is an elevation view of an example of the sequential injection film switch of FIG. 15A after the low pressure switch is opened and before the high pressure switch is opened.

FIG. 15D is an elevation view of an example of the sequential injection film switch of FIG. 15A after both the low pressure switch and the high pressure switch are opened.

FIGS. 19A through 19C is a flowchart of a method for performing fluid analysis using the cartridge-based system of FIG. 17.

FIGS. 20A through 20C is a flowchart of acts performed by the electronic during the method of FIGS. 19A through 19C.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
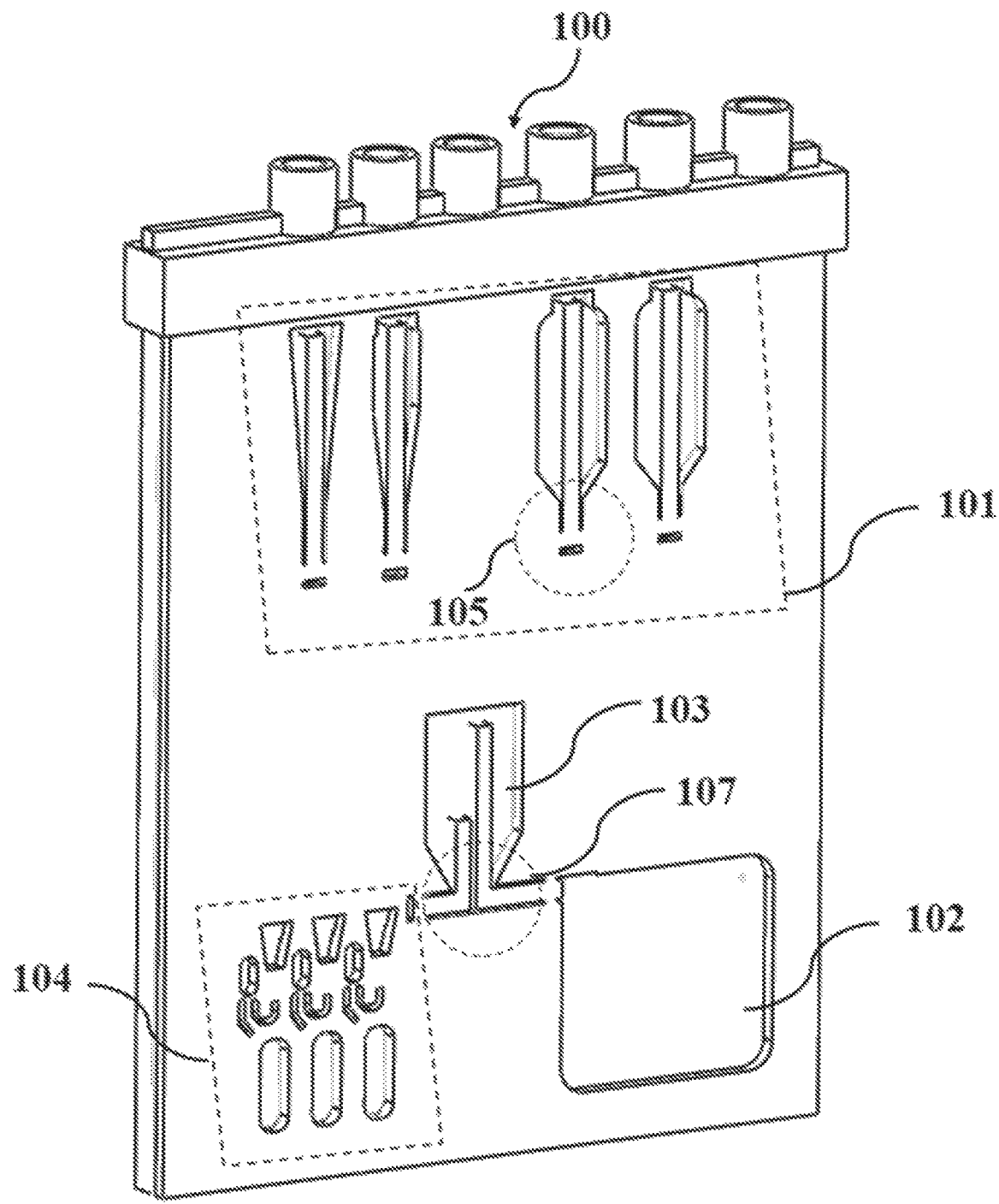
FIG. 1 is a perspective view of a pneumatic-driven fluid cartridge according to one embodiment.

FIG. 1 illustrates an example of an automatic pneumatic-driven cartridge for fluid analysis and/or testing. The cartridge 100 includes a reagent pre-store area 101, a waste collection area 102, a mixing/binding area 103, and a metering/reacting area 104. As described in further detail below, in some implementations, the reagent pre-store area 101 includes multiple separate reagent chamber each with a switchably controlled valve 105 to facilitate liquid flow from each reagent chamber into a mixing chamber of the mixing/binding area 103. Similarly, another two-direction switchable valve 107 is configured to control liquid flow from the mixing/binding area 103 into the waste collection area 102 and/or the metering/reacting area 104.

In the example of FIG. 1, the switchable valves between chambers in the cartridge utilize film-lever actuated switch technology (FAST) to manipulate the on-off state of the liquid flow. As described in further detail below, the FAST switch includes a block, an elastic film, and a lever which is connected to the cover by a hinge. In a non-pressurized state, the lever applies a force to the elastic film which, in turn, presses against the block to form a sealed chamber. However, when a sufficient amount of air pressure is applied to the chamber, the elastic film is expanded and pushes the lever away from the block. In this way, a channel is formed between the block and the elastic film so that liquid can flow into the next chamber.

Figure 2:
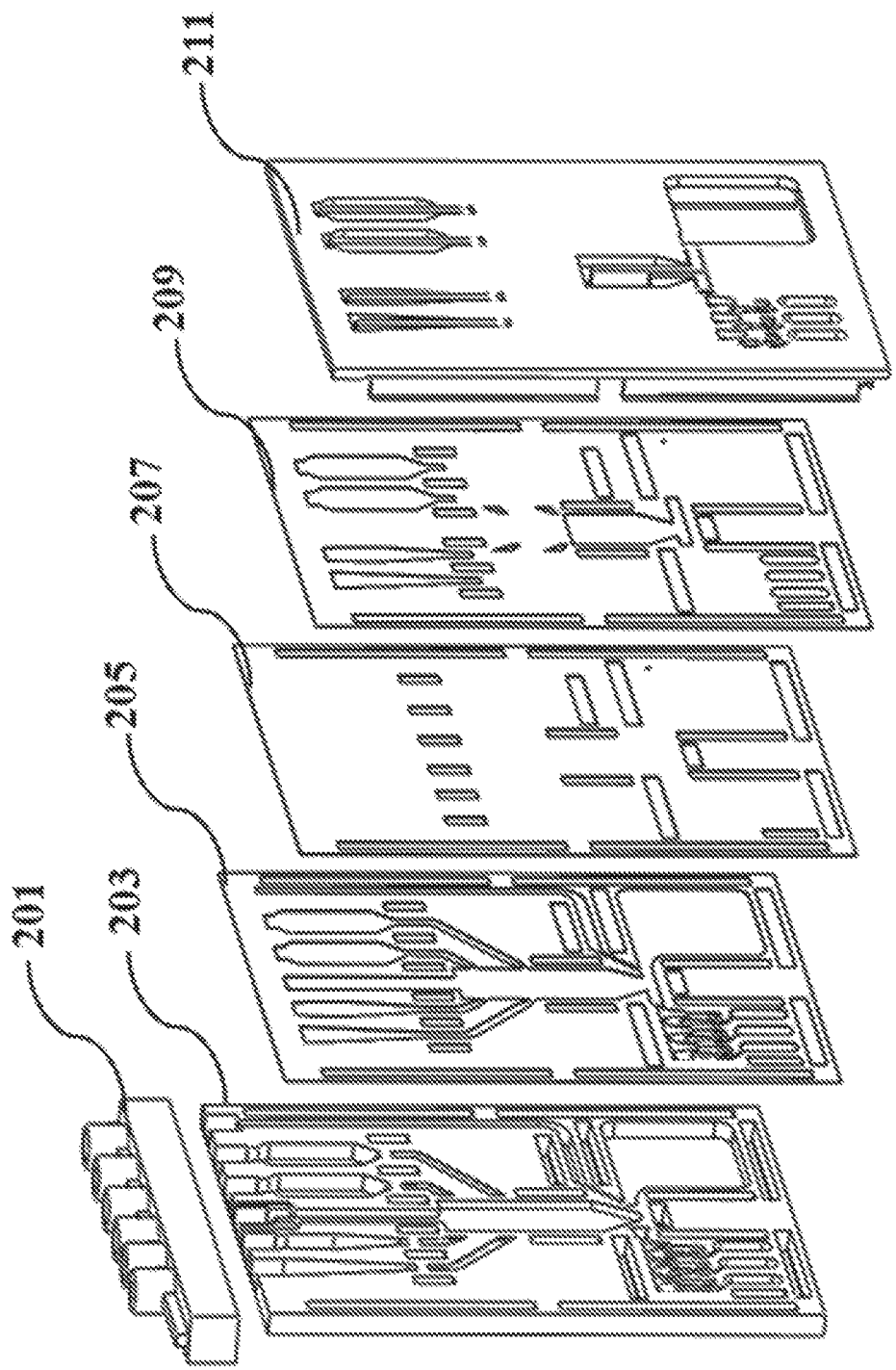
FIG. 2 is an exploded view of the cartridge of FIG. 1.

As illustrated in FIG. 2, the cartridge 100 is a layered structure including a substrate layer 203, an adhesive film layer 205, an elastic layer 207, a plastic film layer 209, and an actuator layer 211. The plastic film layer 209 adheres to the elastic layer 207 and, on an opposite side of the elastic layer 207, the elastic layer 207 is adhered to the substrate layer 203 by the adhesive layer 205. In this example, the actuator layer 211 provides the exterior surface of the cartridge 100 and, accordingly, operates as a "cover" of the cartridge 100. As described in further detail below, the actuator layer 211 is coupled to the substrate layer 203 through an assembly leg and groove mechanism.

As described further below, various chambers and fluid channels are formed in the surface of the substrate layer 203. The top surface of these chambers and fluid channels is sealed by the elastic layer 207 via the adhesive layer 205. However, to allow liquid and/or pneumatic flow into the cartridge, some of the fluid channels extend through a top edge of the substrate layer 203 and are not sealed by the elastic layer 207. Instead, a connector structure 201 couples to the other layers at the top edge. The connector structure 201 includes a plurality of "ports" that can then be coupled to a pneumatic pumping system for controlling the operation of the cartridge as described further below. The connector structure 201 is also formed to enclose the top edge of the assembled layers to provide an additional mechanism for securing the layers to each other.

In some implementations, the substrate layer 203, the actuator layer 211, and the connector 201 are formed of a rigid plastic material (e.g., via injection molding). The size of these components and the chambers/fluid channels formed in the substrate layer 203 can be varied in different implementations based on the volume of liquid to be contained in each chamber. The thickness of the adhesive film layer 205, the elastic layer 207, and the plastic film layer 209 can also vary in different implementations, for example, from several microns thick to hundreds of microns thick. In some implementations, the adhesive film layer 205 is an acrylic material and the elastic layer 207 and the plastic film layer 209 are both clear films.

Figure 3A:
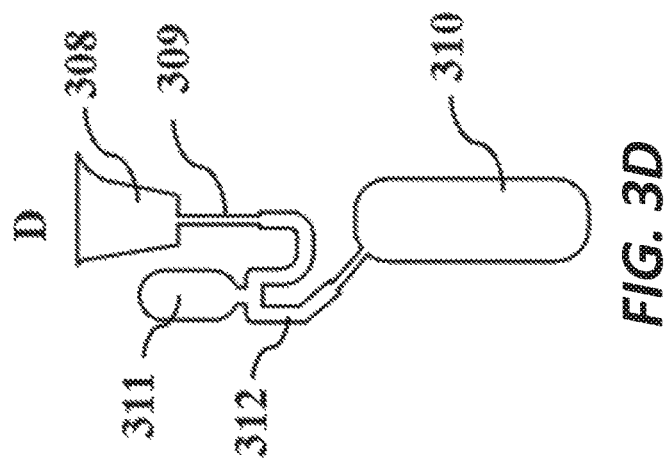
FIG. 3A is an elevation view of the substrate layer of the cartridge of FIG. 2.

One example of the chambers and fluid channels formed in the substrate layer 203 are illustrated in FIG. 3A. In this example, the chambers and fluid channels are formed in a surface of the substrate layer 203 and do not extend completely through the thickness of the substrate layer 203. Accordingly, when the elastic layer 207 is adhered to the surface of the substrate layer 203, the chambers and fluid channels become sealed at the top surface of the substrate layer 203.

Figure 3B:
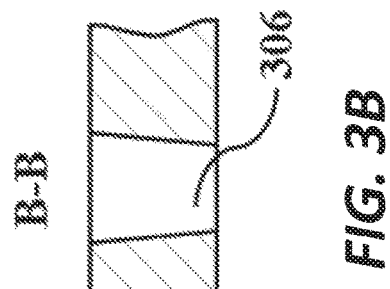
FIG. 3B is a cross-sectional view of an assembly groove of the substrate layer of FIG. 3A.
Figure 3C:
FIG. 3C is a cross-sectional view of a block area of the substrate layer of FIG. 3A.

As illustrated in the example of FIG. 3A, the substrate layer 203 includes a plurality of reagent chambers 301 formed near the top edge of the substrate layer 203 each with openings extending beyond the edge of the substrate layer 203. Each reagent chamber 301 is coupled to a mixing chamber 314 by an injection channel 304. The injection channel 304 is separated from the reagent chamber 301 by a block area 302 formed in the substrate layer 203. A cross-sectional view of the block area 302 along line C-C in FIG. 3A is illustrated in further detail in FIG. 3C. As shown in FIG. 3C, the injection channel 304 has a shallower depth than the reagent chamber 301 to allow for a controlled flow rate of fluid from the reagent chamber 301. Also, the block area 302 also includes a sloped surface 303 extending into the reagent chamber 301 to minimize residuals left in the reagent chamber 301 when the FAST switch is opened at the block 302 (as described below). Another block area 313 is formed in the substrate layer 203 separating the mixing chamber 314 from the waste collection chamber 315 and separating the mixing chamber 314 from the metering chamber 308.

In the example of FIG. 3A, the mixing chamber 314 is positioned below the reagent chambers 301 to allow gravity to provide the motive force for fluid flow, but also includes a channel extending to the top edge of the substrate layer 203 to allow fluid and pneumatic pressure to be applied to the mixing channel. The substrate layer 203 also includes a pair of air outlet channel 307 extend from the channel of the mixing chamber 314 to the top edge of the substrate layer 203 to allow air to escape and to relieve excess pneumatic pressure from the cartridge 100. Similarly, an air flow channel 305 is formed in the substrate layer 203 extending from a location within the waste collection chamber 315 near the block area 313 to the top edge of the substrate layer 203. As described in further detail below, the air flow channel 305 can be used to provide a mixing force for fluids in the mixing chamber 314 and to help control flow of fluids into the metering chamber 308.

The substrate layer 203 also includes assembly grooves 306 through which the assembly legs of the actuator layer will engage to couple the substrate layer 203 to the actuator layer 211. The cross-sectional shape of the assembly grooves 306 in this example along line B-B in FIG. 3A is illustrated in further detail in FIG. 3B.

Figure 3D:
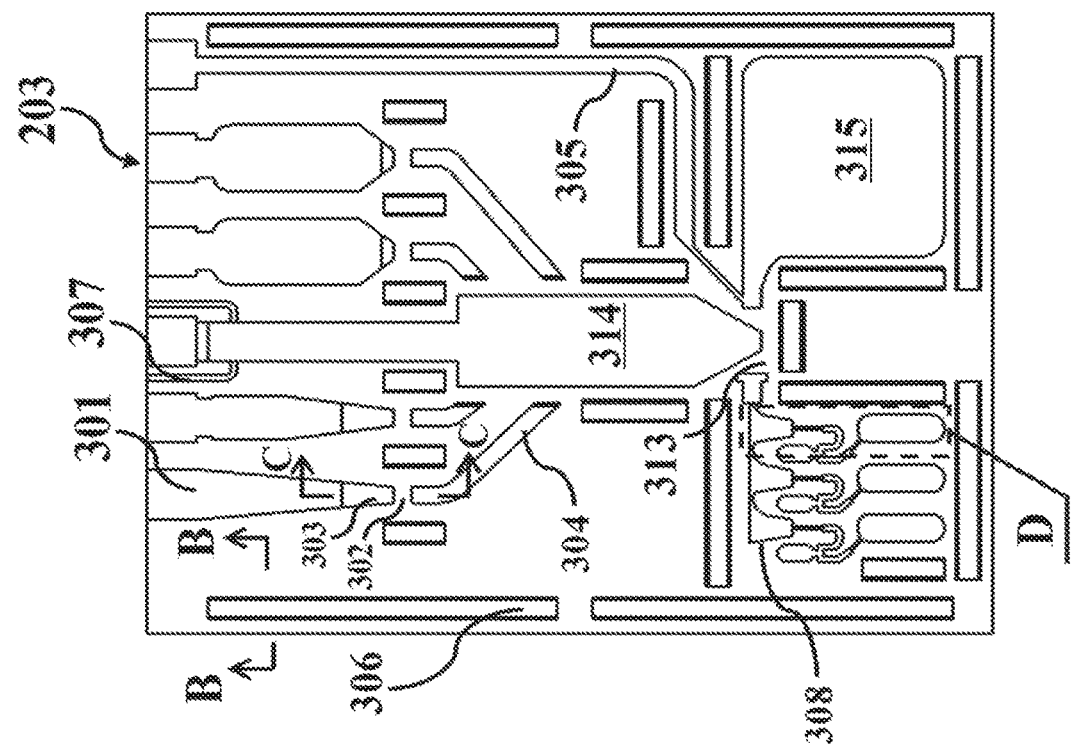
FIG. 3D is a detailed elevation view of a metering/reacting chamber of the substrate layer of FIG. 3A.

Finally, a detailed example of the metering/binding mechanism in the dashed box D of FIG. 3A is shown in FIG. 3D. As shown in FIG. 3D, the metering chamber 308 includes three different sections with a narrow channel 309 extending from each section of the metering chamber 308. Fluid in the metering chamber 308 must pass through the narrow channel 309 to reach the reacting chamber 310. The narrow channel 309 provides a larger liquid resistance that allows pneumatic pressure to more accurately control the flow of fluid into each reacting chamber 310. For example, as discussed further below, because a greater pneumatic pressure is needed to push the fluid from the metering chamber 308 through the narrow channel 309 into the reacting chamber 310, the system can be configured to wait until the fluid fills all three sections of the metering chamber 308 before pushing the fluid through the narrow channels 309 into the reacting chambers 310. In this way, a measured amount of fluid (as dictated by the size of each section of the metering chamber 308) is controllably added into each reacting chamber 310.

Each reacting chamber 310 also has a corresponding sealing material chamber 311 and a sealing channel 312. The sealing channel 312 is positioned to couple the narrow channel 309 to the reacting chamber 310 and the sealing material chamber 311 is positioned to open into the sealing channel 312. As described further below, in some examples, the sealing material chamber 311 of the cartridge 100 is pre-loaded with a phase change material such as, for example, paraffin wax. In some implementations, the cartridge 100 is operated to cause the phase change material to flow from the sealing material chamber 311 into the sealing channel 312 in a liquid form. In some implementations, the phase change material is transformed back into a solid after reaching the sealing channel 312 and seals the reacting chamber 310 as a solid "plug." For example, as described further below, a heating element in the cartridge can be operated to melt a paraffin wax material in the sealing material chamber 311 and the wax will return to solid form once it is allowed to cool in the sealing channel 312. However, in other implementations, the phase change material might not need to be transformed back into a solid state after reaching the sealing channel 312 and instead seals the reacting chambers 310 as a liquid "plug." For example, in some implementations, the cartridge 100 is configured to maintain the materials in the reacting chambers 310 at an elevated temperature during the reaction (e.g., by operating a heater of the cartridge 100). In some such implementations, the phase change material such as, for example, paraffin wax remains in the liquid state in the sealing channel 312, but does not react with the reagents within the reacting chambers 310.

Figure 5:
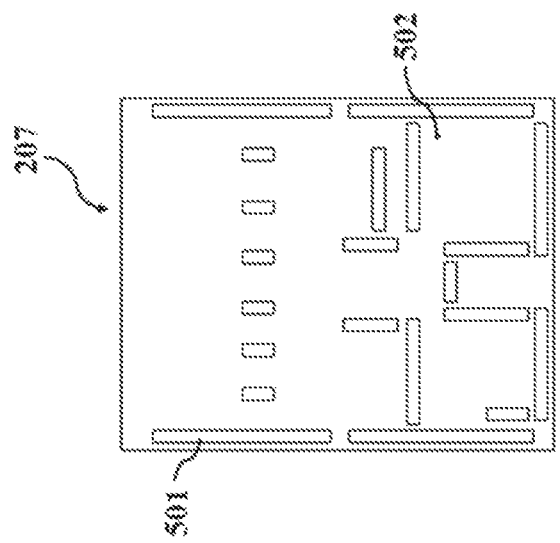
FIG. 5 is an elevation view of an elastic film layer of the cartridge of FIG. 2.
Figure 4:
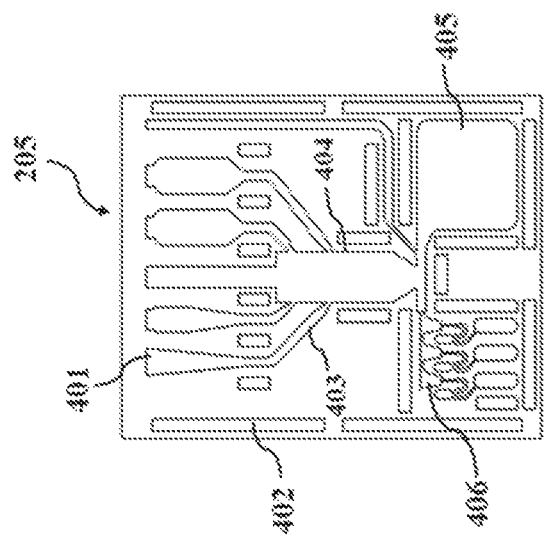
FIG. 4 is an elevation view of an adhesive layer of the cartridge of FIG. 2.

FIG. 4 illustrates an example of the adhesive film layer 205 in further detail. The adhesive film layer 205 includes cut-through patterns around the shape of the reagent chambers 401, the shape of the assembly grooves 402, the shape of the injection channels 403, the shape of the mixing chamber 404, the shape of the waste collection chamber 405, and the shape of the metering and reacting chambers and channels 406. FIG. 5 illustrates an example of the elastic layer 207. The elastic layer 207 includes cut-through patterns corresponding to the shape of the assembly groove 501 and for an air outlet hole 502.

Accordingly, when the adhesive film layer 205 couples the elastic layer 207 to the substrate layer 203, the cut-through patterns formed in the adhesive film layer 205 do not adhere the elastic layer 207 to the block areas which separate the chambers from other chambers. In this way, as described below, fluid flow between chambers can be controlled using pneumatic pressure to expand the elastic layer and to allow fluid flow from one chamber to another between the block area and the elastic layer.

Figure 6:
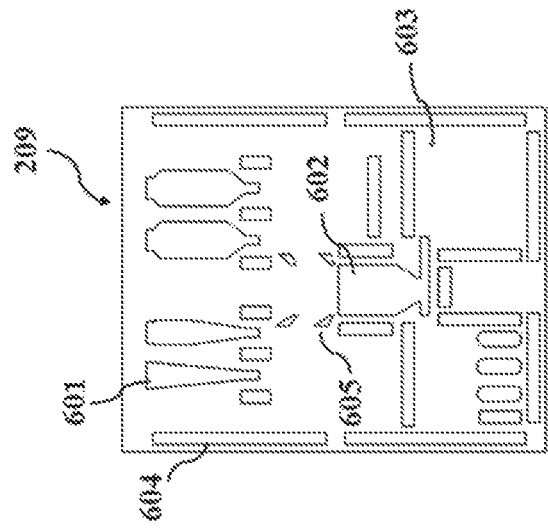
FIG. 6 is an elevation view of a plastic film layer of the cartridge of FIG. 2.

FIG. 6 illustrates an example of the plastic film layer 209 in further detail. The plastic film layer includes cut-through patterns formed in the shape of the reagent chambers 601, the shape of the mixing chamber 602, the shape of the air outlet hole 603, the shape of the assembly grooves 604, and the shape of the injection inlet 605.

Figure 7A:
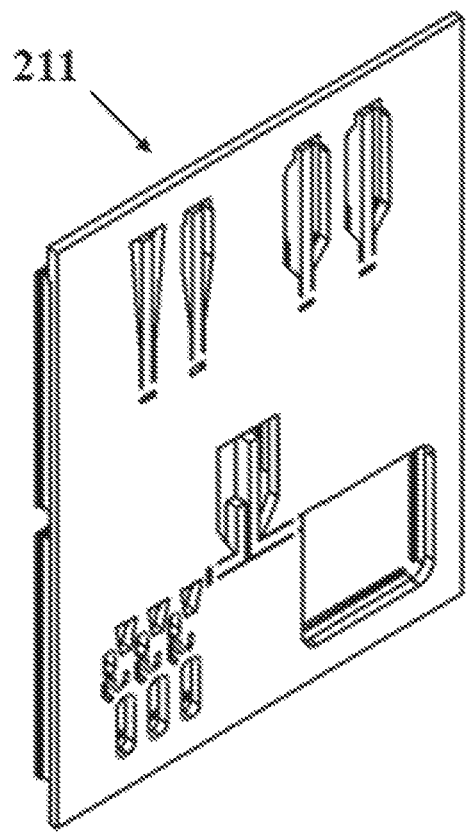
FIG. 7A is a perspective view of a front side of an actuator/cover layer of the cartridge of FIG. 2.
Figure 7B:
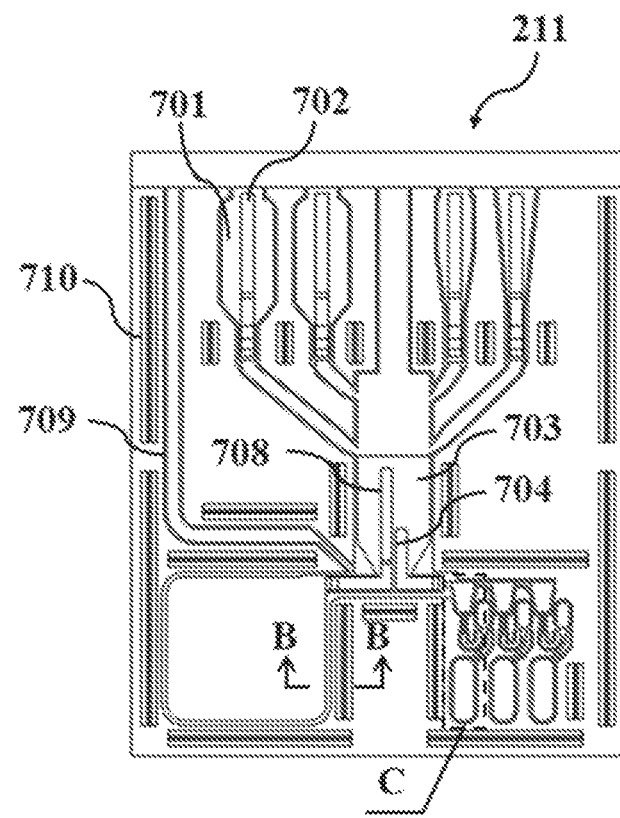
FIG. 7B is an elevation view of a rear side of the actuator/cover layer of FIG. 7A.
Figure 7C:
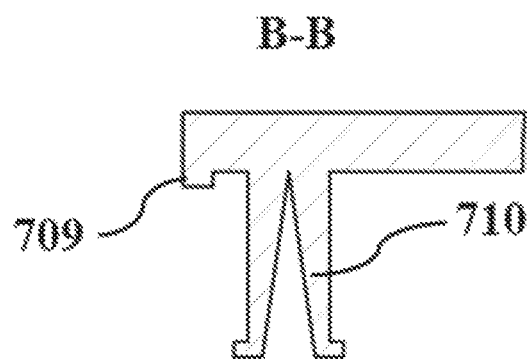
FIG. 7C is a cross-sectional view of an assembly leg of the actuator/cover layer of FIG. 7B.
Figure 7D:
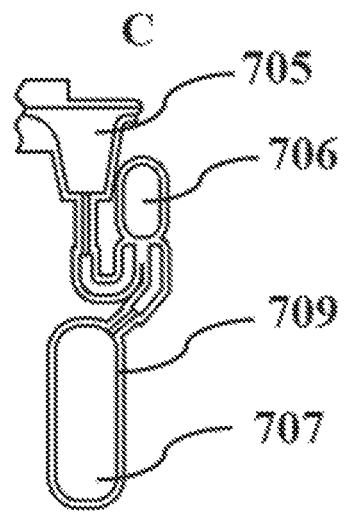
FIG. 7D is a detailed elevation view of a series of windows in the actuator/cover layer of FIG. 7B for viewing the metering and reacting chambers in the substrate layer of FIG. 3B.

FIGS. 7A through 7D illustrate an example of the actuator layer 211 of the cartridge 100. FIG. 7A shows the exterior surface of the actuator layer 211 and FIG. 7B shows the interior surface that is positioned to face the other layers of the cartridge 100. As shown in FIG. 7B, the actuator layer 211 includes a cut-through window in the shape of each reagent chamber 701 with a lever 702 extending into the reagent chamber window 701. Similarly, the actuator layer 211 includes a cut-through window generally in the shape of the mixing chamber 703 with two levers—a high pressure lever 704 and a low pressure lever 708—extending into the mixing chamber. The high pressure lever 703 is shorter than the low pressure lever 708 and, as described further below, the relative length of the lever regulates the pneumatic pressure that will be required to displace the lever to achieve fluid flow.

The actuator layer 211 also includes a cut-through window formed in the shape of the metering and reacting mechanism. This window (indicated with the dashed box C in FIG. 7B) is shown in further detail in FIG. 7D and includes a metering window 705 in the shape of the metering chamber 308, a sealing material window 706 in the shape of the sealing material chamber 311, and a reacting chamber window 707 in the shape of the reacting chamber 310. In some implementations, the window formed in the actuator layer 211 may also includes a window in the shape of the narrow channel 309 and the sealing channel 312 to allow a user to view the movement of fluid and sealing material through these channels during use of the cartridge.

The actuator layer 211 also includes an arrangement of assembly protrusions 709 and assembly legs 710. An example of an assembly protrusion 709 and an assembly leg 710 (along line B-B in FIG. 7B) is illustrated in detail in FIG. 7C. As described above, when the cartridge 100 is assembled, the assembly legs 710 extend through the assembly groove shape cut-out 604 of the plastic layer 209, through the assembly groove shape cut-out 501 of the elastic layer 207, through the assembly groove shape cut-out 402 of the adhesive film layer 205, and through the assembly grooves 306 of the substrate layer 203. The assembly legs 710 then engage the substrate layer 203 on the opposite side of the assembly grooves 306 to secure the actuator layer 211 to the substrate layer 203. The assembly protrusions 709 act as a spacer between the layers when the cartridge 100 is assembled.

Figure 8A:
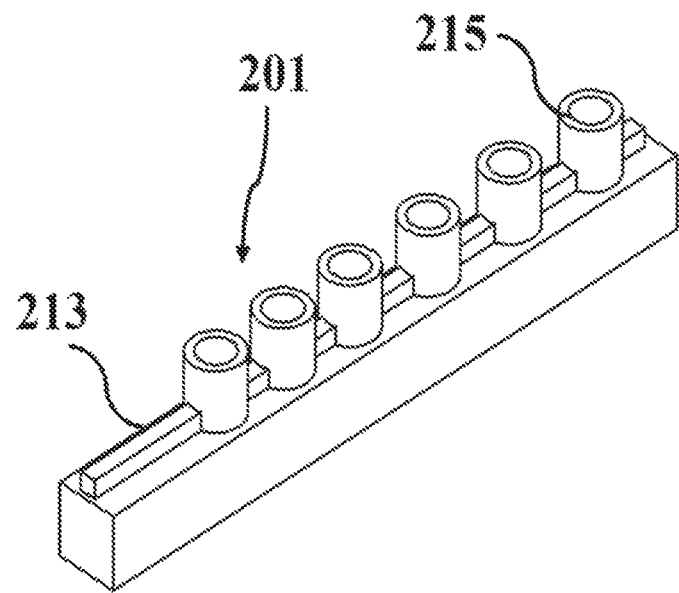
FIG. 8A is a perspective view of a top side of a connector structure of the cartridge of FIG. 2.
Figure 8B:
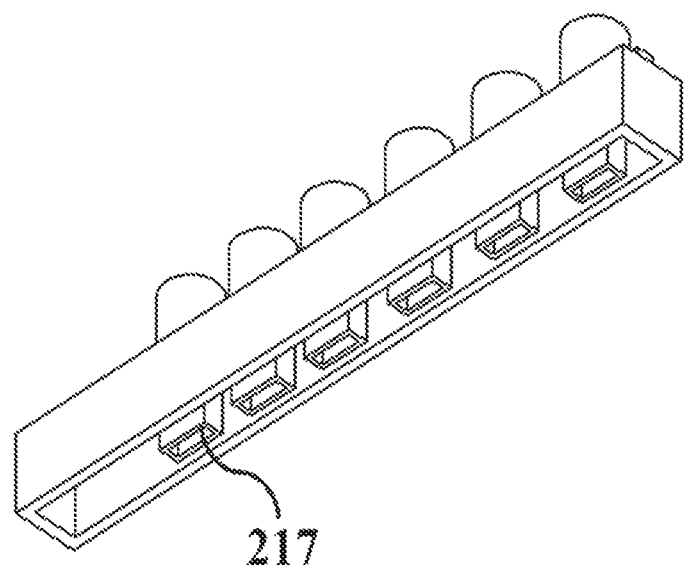
FIG. 8B is a perspective view of the underside of the connector structure of FIG. 8A.

FIGS. 8A and 8B illustrate and example of the connector structure 201. The connector structure 201 includes a stiffener 213 formed in the shape of a raised line extending along the length of the top surface of the connector structure 201 to provide additional structural stiffness for the connector structure 201. Multiple connector ports 215 are formed in the top surface of the connector structure 201, which each extend to a plug 217 extending form the bottom of the connector structure 201. The plugs 217 are each formed to fit within a channel or chamber that is formed to open through the top edge of the substrate layer 203. An opening for pneumatic air and/or fluid extends through each connector port 215 and its corresponding plug 217. Once the cartridge 100 is assembled, the connector ports 215 are used to introduce fluid and/or regulate pneumatic pressures within the chambers of the cartridge 100 as described in further detail below.

In one example of the cartridge 100 of FIG. 1, the dimensions of the substrate layer 203 are 113 mm wide, 138 mm tall, and 5 mm thick; the dimensions of the adhesive film layer 205 are 113 mm wide, 138 mm tall, and 0.18 mm thick; the dimensions of the elastic layer 207 are 113 mm wide, 138 mm tall, and 0.3 mm thick; the dimensions of the plastic film layer 209 are 113 mm wide, 138 mm tall, and 0.1 mm thick; the dimensions of the actuator layer 211 are 113 mm wide, 138 mm tall, and 2 mm thick; and the dimensions of the connector structure 201 are 118 mm wide, 22 mm tall, and 11 mm thick. In this example, the substrate layer 203, the actuator layer 211, and the connector structure 201 may each be formed of a polylactic acid (PLA) material, a poly(methyl methacrylate) (PLMA) material, or another thermoplastic material; the plastic film layer 209 may be formed of a polyethylene terephthalate (PET) material; the adhesive film layer 203 may be formed of an acrylic material; and the elastic layer 207 may be formed of a polydimethylsiloxane (PDMS) material. However, other materials and other dimensions may be used in other implementations.

Additionally, this example of the cartridge 100 of FIG. 1 described above, the lever 702 for each reagent chamber 701 is 37 mm long, the low pressure lever 708 is 28 mm long, and the high pressure lever 704 is 14 mm long. Because, in this example, each lever 702 is longer than the low pressure lever 708, the internal pressure of the reagent chamber 301 necessary to outwardly bend each lever 702 is less than the internal pressure of the mixing chamber 314 that would be necessary to outwardly bend the low pressure lever 708. Accordingly, in some implementations, a system configured to operate the cartridge 100 of this example may be configured to apply the same pressure P to different connector ports of the connector structure 201 to operate the levers 702 and the low pressure lever 708. However, in other implementations, different pressures may be applied to operate levers of different lengths and levers of other lengths may also be used in addition to or instead of the levers describes in the example above.

Figure 9A:
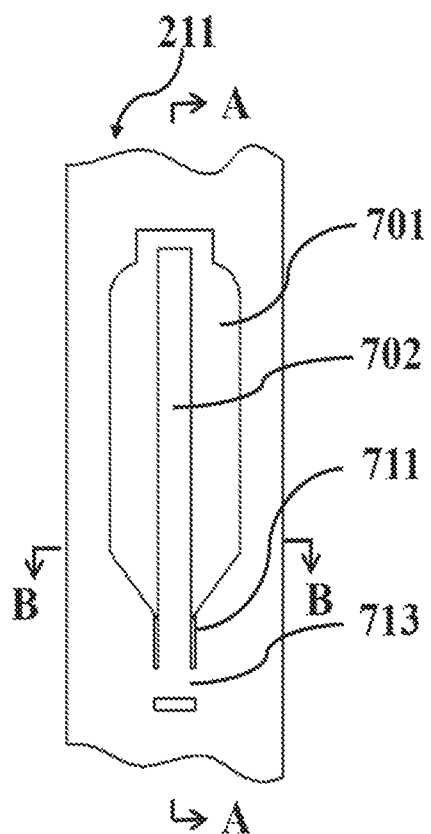
FIG. 9A is an elevation view of a pneumatic-pressure-activated film switch in the cartridge of FIG. 1.
Figure 9B:
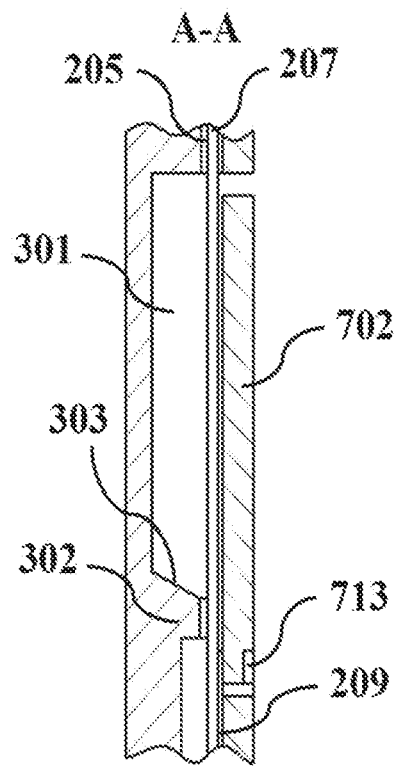
FIG. 9B is a first cross-sectional view of the pneumatic-pressure-activated film switch of FIG. 9A.
Figure 9C:
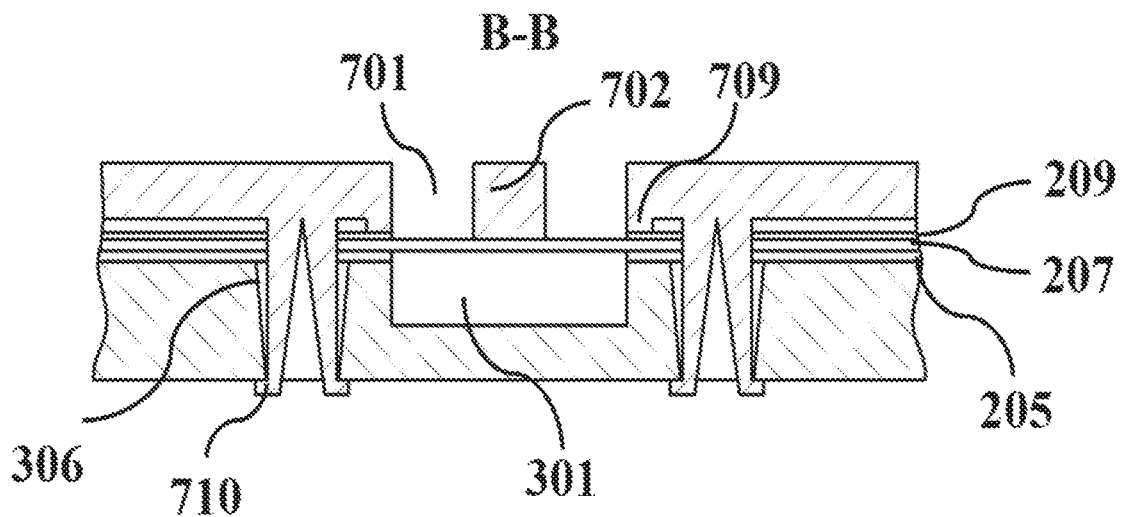
FIG. 9C is a second cross-sectional view of the pneumatic-pressure-activated film switch of FIG. 9A.

FIGS. 9A through 9C illustrate an example of the FAST switch/valve mechanism in the assembled cartridge 100. FIG. 9A shows the exterior surface of the actuator layer 211 at one of the reagent window cut-outs 701. As described above, a lever 702 of the actuator layer 211 extends into the reagent window cut-out 701. In some implementations, the lever 702 may be a separate component coupled to the actuator layer 211 by a hinge. However, in the example of FIG. 9A, the lever 702 is integrally formed as a part of the actuator layer 211 by cutting out the shape of the lever 702 along with the reagent window cut-out 701. A pair of gaps 711 are also formed in the actuator layer 211 on either side of the lever 702 across an area corresponding to the block area 302 to allow the lever 702 to extend across the block area 302 and into the area of the reagent chamber 301. In this way, as described further below, pressures within the reagent chamber 301 that are sufficient to inflate the elastic layer 207 cause the lever 702 to bend outward at the hinge area 713 opening a channel between the block 302 and the elastic layer 207.

FIG. 9B illustrates a cross-sectional view of the assembled cartridge 100 along line A-A in FIG. 9A. FIG. 9C illustrates a cross-sectional view along line B-B in FIG. 9A. As described above and as illustrated in the example of FIGS. 9A through 9C, when the cartridge 100 is assembled, the elastic layer 207 is adhered to the substrate layer 203 by the adhesive film layer 205. The assembly leg 710 is bent during assembly to fit through the V-shaped assembly groove 306 to engage the actuator layer 211 to the substrate layer 203 as illustrated in FIG. 9C. As also illustrated in FIG. 9C, the assembly protrusions 709 of the actuator layer 211 press against the elastic layer 207 to further secure the seal between the elastic layer 207 and the substrate layer 203.

FIGS. 10A and 10B illustrate an example of the operating principle of the FAST switch/valve. Because the lever 702 is formed as a part of the actuator layer 211, its equilibrium position causes the lever 702 to apply a sealing force to the elastic layer 207 at the area of the reagent chamber 301 and the block 302. This sealing force applied by the lever 702 limits or prevents fluid flow between the block 302 and the elastic layer 207 as shown in the example of FIG. 10A. However, controllably increasing the pressure within the reagent chamber 301 causes the elastic layer 207 to inflate in the area of the reagent chamber 301 and, when the internal pressure within the reagent chamber 301 reaches a certain level, the inflation of the elastic layer 207 will cause the lever to bend outwardly away from the substrate layer 203. As illustrated in FIG. 10B, this outward bending of the lever 702 opens a channel 715 between the block 302 and the elastic layer 207 through which fluid is able to flow. Accordingly, the FAST switch/valve is opened by increasing the internal pressure within the reagent chamber. As described in further detail below, in some implementation, the cartridge 100 is operated by using a pneumatic pump to regulate and adjust the internal pressure within the various chambers.

The FAST switch/valve as illustrated in the example of FIGS. 10A and 10B provides robustness to fluid handling systems because the liquid stored in the chamber will not experience unexpected and unintended flow into another chamber due to vibration. Instead, only applying the proper air pressure can make the liquid flow from one chamber to another. Furthermore, the FAST switch/valve provides for on-demand injection. The FAST switch/valve responds quickly to applied air pressure and, when the increased air pressure is removed, the liquid flow stops simultaneously.

Although FIGS. 10A and 10B illustrate the principle of operation, the specific function of the FAST switch/valve can be adjusted and tuned for specific functionality by adjusting the size and/or shape of the lever. For example, different lever lengths (as illustrated in FIG. 11) can be used to define the pressure required to open the FAST switch/valve. As illustrated in the graph of FIG. 12, the pressure required to open the FAST switch/valve increases as the length of the lever decreases.

Figure 13C:
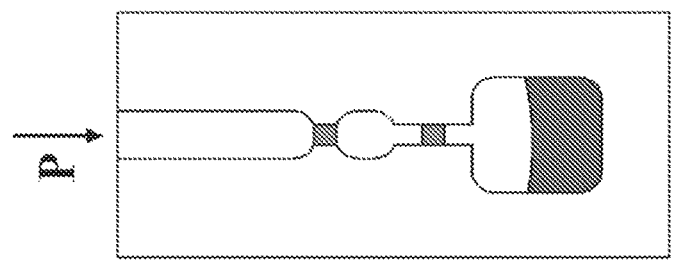
FIG. 13C is an elevation view of an example of the cascade injection film switch of FIG. 13A after the switch is opened.
Figure 13B:
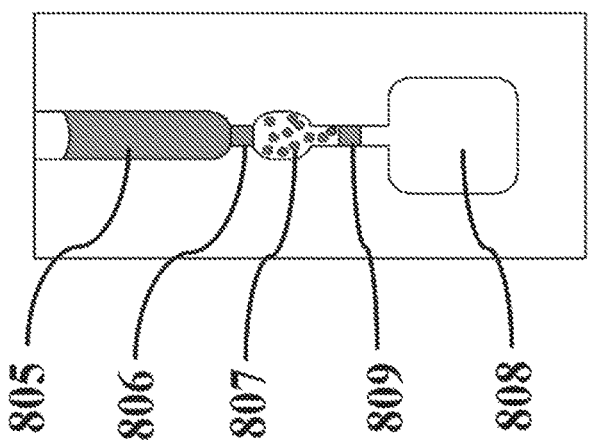
FIG. 13B is an elevation view of an example of the cascade injection film switch of FIG. 13A before the switch is opened.
Figure 13A:
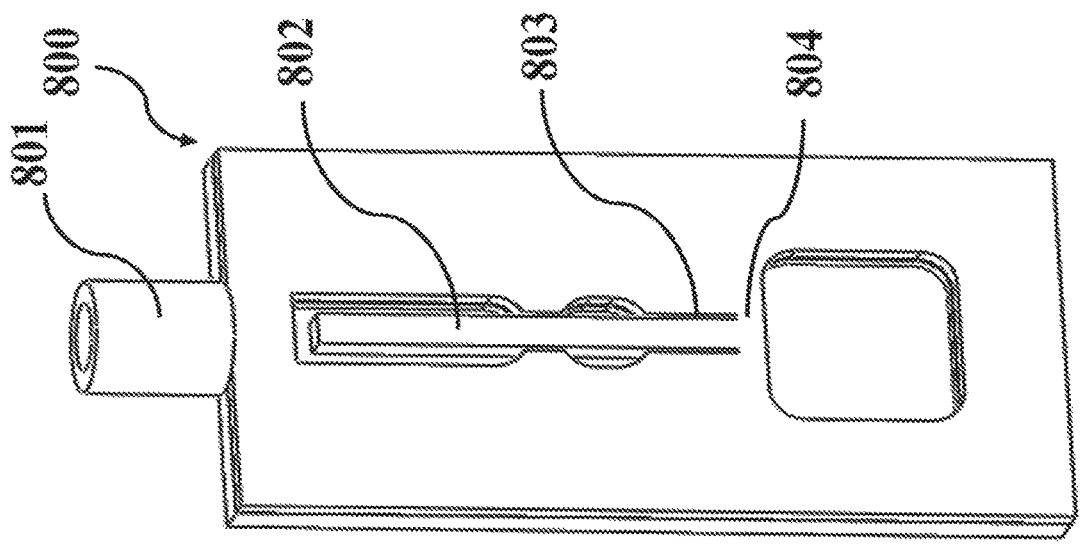
FIG. 13A is a perspective view of a cascade injection film switch according to one embodiment.
Figure 14C:
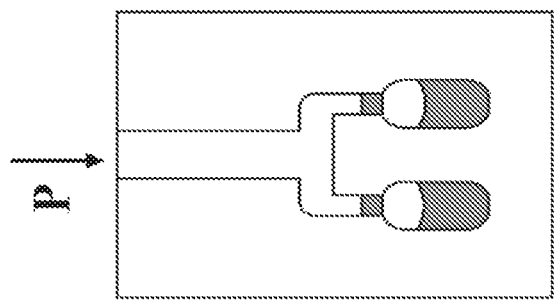
FIG. 14C is an elevation view of an example of the simultaneous injection film switch of FIG. 14A after the switch is opened.
Figure 14B:
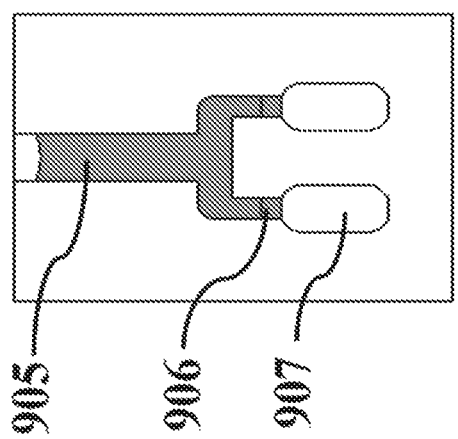
FIG. 14B is an elevation view of an example of the simultaneous injection film switch of FIG. 14A before the switch is opened.
Figure 14A:
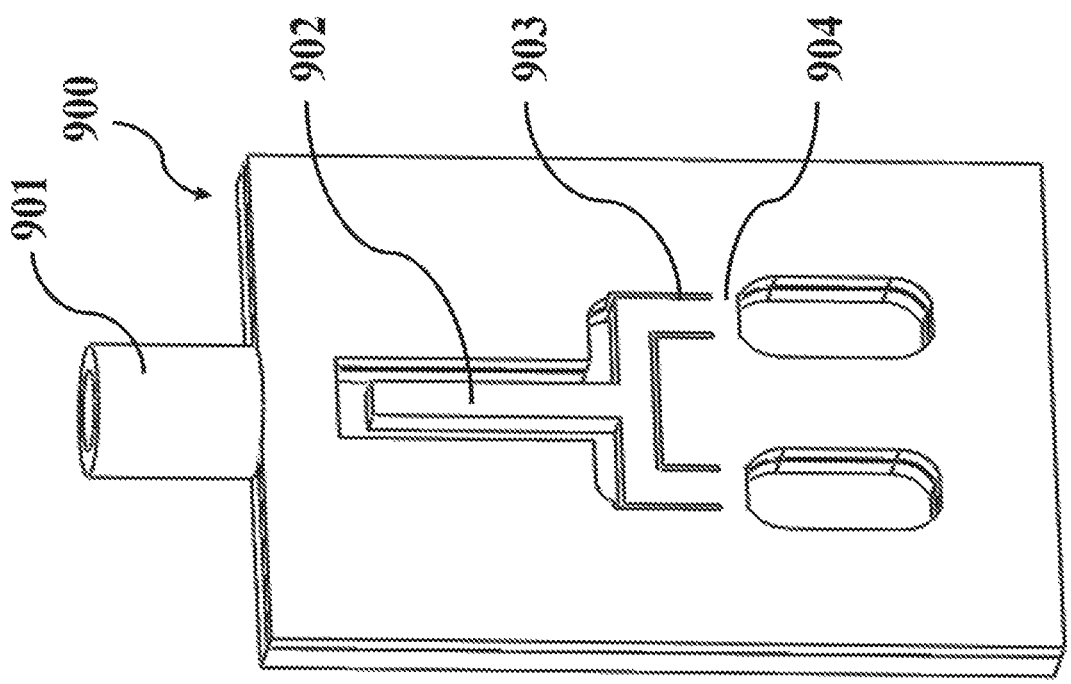
FIG. 14A is a perspective view of a simultaneous injection film switch according to one embodiment.

Additionally, due to the adjustable open pressure properties illustrated in FIGS. 11 and 12, devices can be designed, for example, to utilize FAST switches/valves to transport fluid in a cascaded sequence of different chambers (e.g., as illustrated in the example of FIGS. 13A through 13C), to transport fluid simultaneously from one chamber into multiple different chambers (e.g., as illustrated in the example of FIGS. 14A through 14C), to transport fluid into different chambers sequentially (e.g., as illustrated in the example of FIGS. 15A through 15D), and to selectively transport fluid into a specific one of multiple different chambers coupled to the chamber in which the fluid resides (e.g., as illustrated in the example of FIGS. 16A through 16D).

FIGS. 13A through 13C illustrate an example of a cascading FAST switch/valve 800 in which fluid controllably moves from a first chamber 805 into second chamber 807 and then moves from the second chamber 807 into the third chamber 808. As illustrated in FIG. 13A, a single cascade lever 802 extends from a hinge area 804 across a second block area 809, across the second chamber 807, across a first block area 806, and partially across the first chamber 805. As described above, gaps 803 are formed in the actuator layer to allow the lever to bend at the hinge area 804 below the second block area 809. As illustrated in FIG. 13B, a sample fluid can be placed in the first chamber 805 through a connector port 801 on the top edge of the cartridge and the second chamber can be pre-loaded with a reagent. When the air pressure P is applied to the connector port 801, the elastic layer pushes the cascade lever 802 causing the cascade lever 802 to bend outwardly opening the channel. The sample fluid can then flow across the first block 806 into the second chamber where it combines with the reagent and then the combined mixture continues to flow across the second block 809 into the third chamber 808.

FIGS. 14A through 14C illustrate an example of a FAST switch/valve 900 configured to simultaneously inject a sample fluid from a first chamber 905 into two separate collection chambers 907. As illustrated in FIGS. 14B, the first chamber 905 is formed in the shape of an inverted Y with two branches. Each lower branch of the first chamber 905 is separated from a respective collection chamber 907 by a block 906. As shown in FIG. 14A, a simultaneous lever 902 is similarly formed in an inverted Y shape extending into the area of the first chamber 905 with gaps 903 cut around the simultaneous lever 902 to allow the simultaneous lever 902 to bend at two hinge areas 904. Each hinge area 904 is positioned below the block 906 of each respective collection chamber 907. A sample fluid is placed in the first chamber 905 through a connector port 901 on the top edge of the cartridge. When the air pressure P is applied to the first chamber 905 through the connector port 901, the elastic film pushes the simultaneous lever 902 causing the simultaneous lever 902 to bend outwardly simultaneously opening channels for both collection chambers 907. The liquid can then flow through both blocks 906 and into both collection chambers 907 simultaneously.

FIGS. 15A through 15D illustrate an example of a FAST switch/valve 1000 configured to sequentially inject a sample fluid from a first chamber 1006 into a first collection chamber 1008 and then from a second chamber 1010 into a second collection chamber 1011 as the applied pressure is increased. As illustrated in FIG. 15B, sample fluids injected through a single connector port 1001 flows into both the first chamber 1006 and the second chamber 1010. The first chamber 1006 is separated from a first collection chamber 1008 by a first block 1007 and the second chamber 1010 is separated from a second collection chamber 1011 by a second block 1012. As illustrated in FIG. 15A, two separate levers are formed in the actuator layer—a low pressure lever 1002 and a high pressure lever 1005. The low pressure lever 1002 is positioned across the second block 1012 and extending partially across the second chamber 1010 with a hinge 1004 positioned below the second block 1012 and with gaps 1003 formed along side the low pressure lever 1002 to allow it to bend at the hinge 1004. The high pressure lever 1005 is similarly positioned above the first chamber 1006.

As illustrated in FIG. 15A, the high pressure lever 1005 and the low pressure lever 1002 are formed with different lengths and, as discussed above, in reference to FIGS. 11 and 12. The relative length of the lever affects the amount of internal pressure required to cause the lever to bend outwardly and open the channel. As illustrated in FIG. 15C, when a first pressure P is applied to the connector port 1001, the elastic film pushes the low pressure lever 1002 causing it to bend outwardly opening a channel from the second chamber 1010 to the second collection chamber 1011. However, the first pressure P is not sufficient to cause the high pressure lever to bend outwardly and, therefore, the sample fluid does not yet flow from the first chamber 1006 into the first collection chamber 1008. When the pressure applied to the connector port 1001 is increased from the first pressure P to a second, higher pressure P', then the elastic film is able to push the high pressure lever 1005 with enough force to cause it to bend outwardly opening the channel from the first chamber 1006 into the first collection chamber 1008.

Figure 16B:
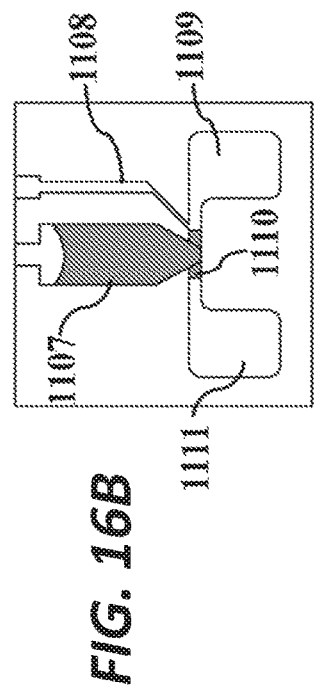
FIG. 16B is an elevation view of the selective injection film switch of FIG. 16A before the low pressure switch or the high pressure switch is opened.

FIGS. 16A through 16D illustrate an example of a FAST switch/valve 1100 configured to selectively inject a sample fluid from a first chamber 1107 into either a first collection chamber 1109 or a second collection chamber 1111 depending on an amount of pressure that is applied to the first chamber 1107. As illustrated in FIG. 16B, the first chamber 1107 is separated from the first collection chamber 1109 and the second collection chamber 1111 by respectively blocks 1110. The first chamber 1107 opens at the top edge of the cartridge through a first connector port 1101. An additional air flow channel 1108 extends from a second connector port 1102 at the top edge of the cartridge to the first collection chamber 1109 at a location near the block 1110 separating the first collection chamber 1109 from the first chamber 1107.

Figure 16C:
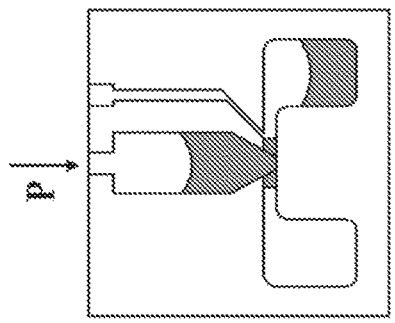
FIG. 16C is an elevation view of the selective injection film switch of FIG. 16A after the low pressure switch is opened and before the high pressure switch is opened.
Figure 16D:
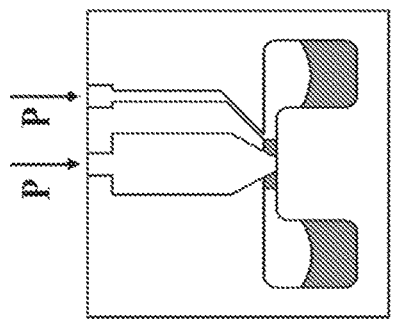
FIG. 16D is an elevation view of the selective injection film switch of FIG. 16A after both the low pressure switch and the high pressure switch are opened.
Figure 16A:
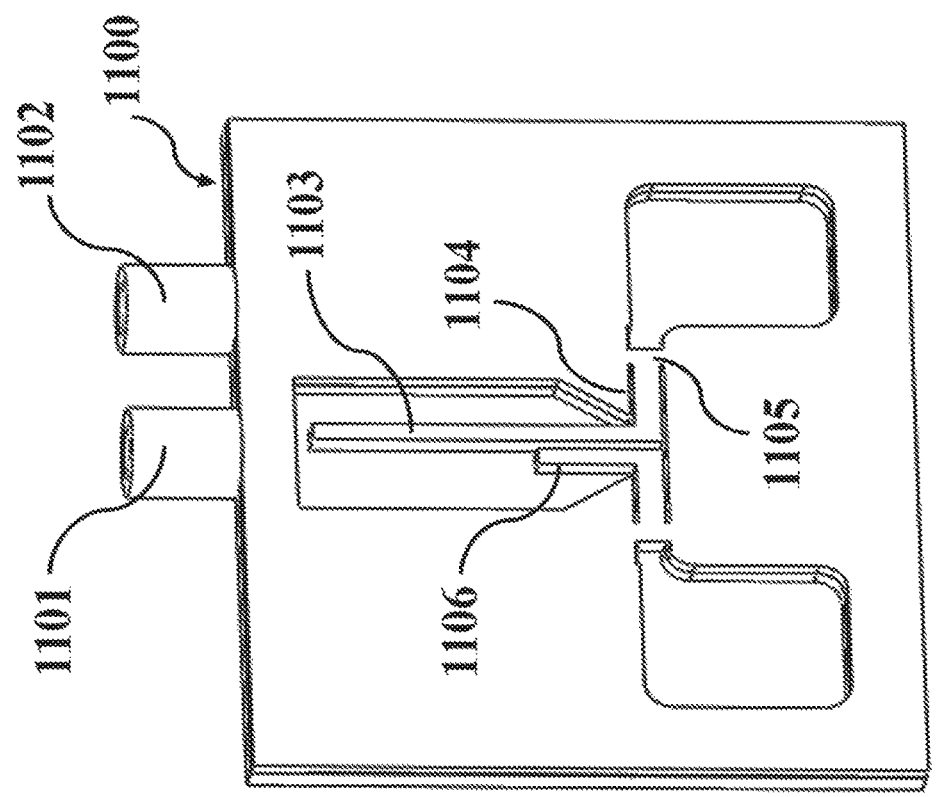
FIG. 16A is a perspective view of a selective injection film switch including a low pressure switch and a high pressure switch according to one embodiment.

As illustrated in FIG. 16A, two levers are formed in the actuator layer of the cartridge—a low pressure lever 1103 and a high pressure lever 1106. Each lever is formed to extend from a respective hinge area 1105 across the respective block area 1110. Gaps 1104 are formed along each lever to allow the lever to bend in response to a sufficient internal pressure within the first chamber 1107. Again, like the example of FIGS. 15A through 15D, the low pressure lever 1103 is longer than the high pressure lever 1106 and, therefore, will bend outwardly and open the respective flow channel in response to a lower internal pressure in the first chamber 1107.

As illustrated in FIG. 16C, when a first air pressure P is applied to the first connector port 1101, the elastic layer inflates sufficiently to push the low pressure lever 1103 with enough force to bend the low pressure lever 1103 outwardly opening the channel from the first chamber 1107 into the first collection chamber 1109. In response, fluid is able to flow from the first chamber 1107 into the first collection chamber 1109. However, the pressure P is not sufficient to outwardly bend the high pressure lever and, therefore, the fluid is not able to flow from the first chamber 1107 into the second collection chamber 1111.

As shown in FIG. 16D, when another air pressure P is applied to the second connector port 1102, a reverse air pressure is applied through the air flow channel 1108 and then from the first collection chamber 1109 into the first chamber 1107. This reverse air pressure flow stops the liquid from flowing from the first chamber 1107 into the first collection chamber 1109. Additionally, the combination of the reverse air pressure P applied to the second connector port 1102 and the original air pressure P applied to the first connector port 1101 together apply enough internal pneumatic pressure on the elastic layer in the first chamber 1107 to push the high pressure lever 1106 with enough force to cause the high pressure lever 1106 to bend outwardly opening the channel from the first chamber 1107 into the second collection chamber 1111. Accordingly, fluid is now able to flow from the first chamber 1107 into the second collection chamber 1111, but is prevented from flowing from the first chamber 1107 into the first collection chamber 1109.

In the example of FIGS. 16A through 16D, the same air pressure P is applied to both the first connector port 1101 and the second connector port 1102 to cause the high pressure lever to bend outwardly. However, in some implementations, the air pressure applied to the second connector port 1102 may be different from the air pressure applied to the first connector port 1101. Similarly, in the example of FIGS. 16A through 16D, the air pressure P applied to the first connector port 1101 is the same when opening both the low pressure lever and the high pressure lever. However, in some implementations, the air pressure applied to the first connector port 1101 may be different when opening the low pressure lever 1103 than when opening the high pressure lever 1106. For example, in some implementations, the system may be configured to apply a first lower pressure P to the first connector port 1101 when opening the low pressure valve and to then apply a second higher pressure P' to the first connector port 1101 when opening the high pressure valve.

Figure 17A:
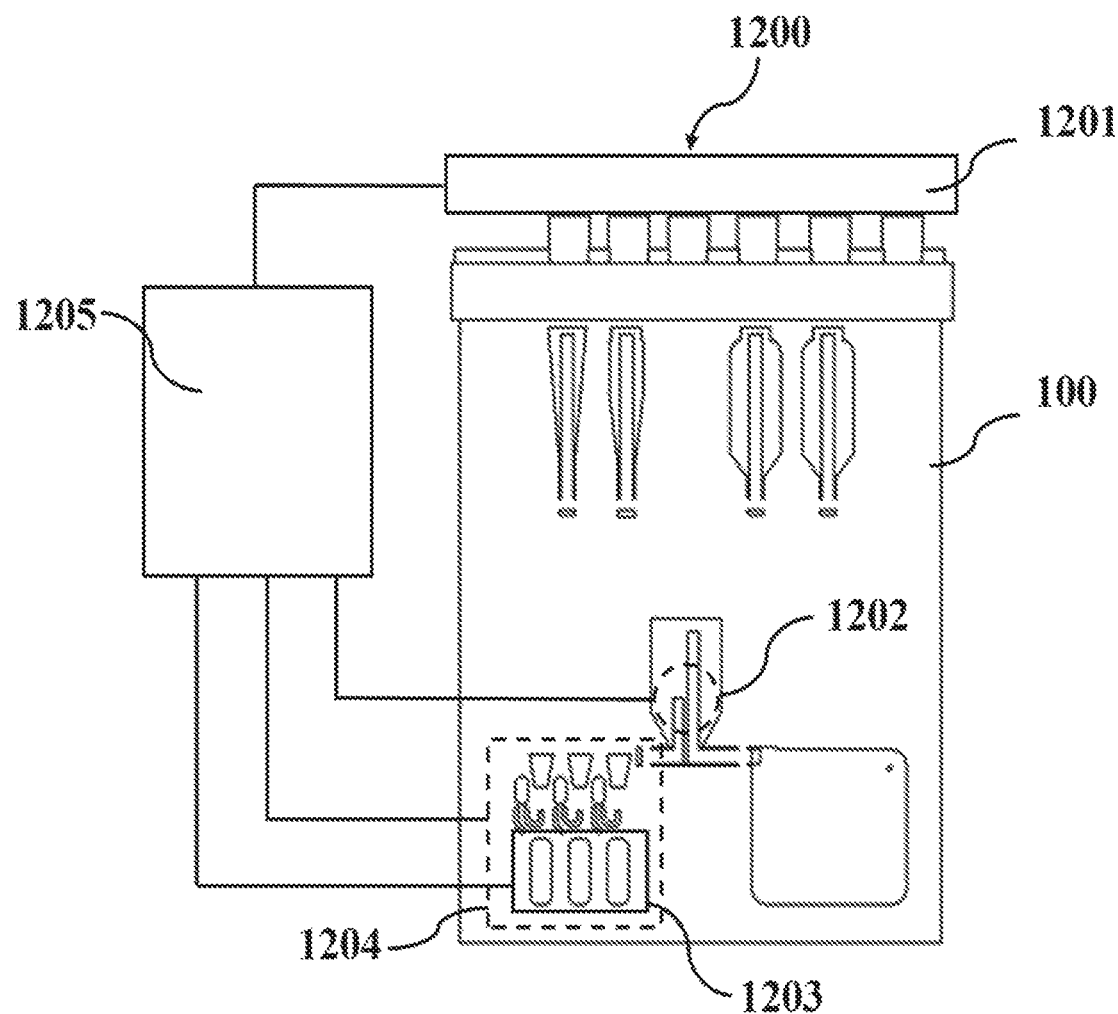
FIG. 17A is an elevation view schematic diagram of a system for performing fluid analysis using the cartridge of FIG. 1.

FIG. 17A illustrates an example of a system 1200 for performing analysis of a fluid sample using the cartridge 100 described above. In some implementations, the system 1200 may be configured to perform polymerase chain reaction (PCR) testing of a sample fluid, for example, to detect whether a particular medical condition is indicated by the analysis of the sample fluid. In this example, the reagent chambers 301 of the cartridge 100 are preloaded with reagents for performing cell lysis, washing, and elution during the PCR reaction process. However, in other implementations, reagents can be loaded into the reagent chambers 301 through the respective connector ports 215 of the connector structure 201 at the time of testing.

As illustrated in FIG. 17A, a pneumatic source 1201 is coupled to the connector ports 215 of the connector structure 201. In the example of FIG. 17A, the pneumatic source 1201 includes a coupler housing with a plurality of connector ports positioned, sized, and configured to interconnect with the connector ports 215 of the connector structure 201 of the cartridge 100. However, in other implementations, the pneumatic source 1201 may be coupled to each connector port 215 by other mechanisms including, for example, multiple separate pneumatic hoses. In this example, the connector structure 201 of the cartridge 100 includes six different connector ports 215 which are labelled in FIG. 17B as the "1st Port," "2nd Port," "3rd Port," "4th Port," "5th Port," and "6th Port." The first connector port is coupled to a reagent chamber pre-loaded with an elution fluid, the second connector port is coupled to a reagent chamber pre-loaded with magnetic beads, the third connector port is coupled to the mixing chamber 314, the fourth connector port is coupled to a reagent chamber pre-loaded with a first washing fluid, the fifth connector port is coupled to a reagent chamber pre-loaded with a second washing fluid, and the sixth connector port is coupled to the waste collection chamber 315 via the air flow channel 305.

Figure 17B:
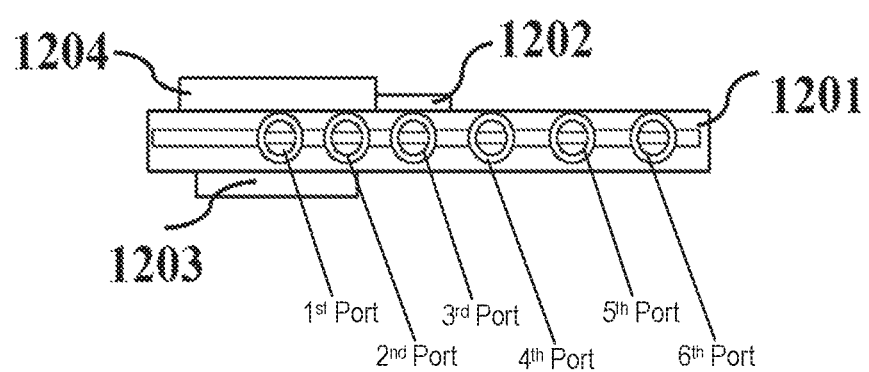
FIG. 17B is an overhead view schematic diagram of the system of FIG. 17A.

As illustrated in the example of FIGS. 17A and 17B, the cartridge 100 further includes an electromagnet 1202, a heater 1204, and a signal detection module/sensor 1203. In this example, the electromagnet 1202 is positioned on the back side of the substrate layer 203 at a location proximate to the mixing chamber 314. Accordingly, the electromagnet 1202 can be controllably activated and deactivated to extract magnetic beads within the mixing chamber 314 and to prevent the magnetic beads from flowing into other chambers of the cartridge 100 (as described further below). In this example, the heater 1204 is coupled to the back side of the substrate layer 201 at a location proximate to the sealing material chambers 311. Accordingly, the heater 1204 can be controllably activated to melt the sealing material within the sealing material chambers 311 and controllably deactivated to allow the sealing material to solidify after it has flowed out of the sealing material chambers 311 into the respective sealing channels 312. Finally, in this example, the signal detection module/sensor 1203 is positioned on a front side of the actuator layer 211 at a location proximate to the reacting chambers 310 and is operated to capture signal data indicative of a condition of the sample material in the reacting chamber 310.

Finally, as illustrated in FIG. 17A, an electronic controller 1205 is communicatively coupled to the pneumatic source 1201, the electromagnet 1202, the signal detection module/sensor 1203, and the heater 1204. As shown in further detail in FIG. 18, the electronic controller 1205 includes an electronic processor 1801 and a non-transitory computer-readable memory 1803. The memory 1803 stores data and instructions that, when executed by the electronic processor 1801 provide the functionality of the electronic controller 1205 including, for example, the functionality as described herein.

Figure 18:
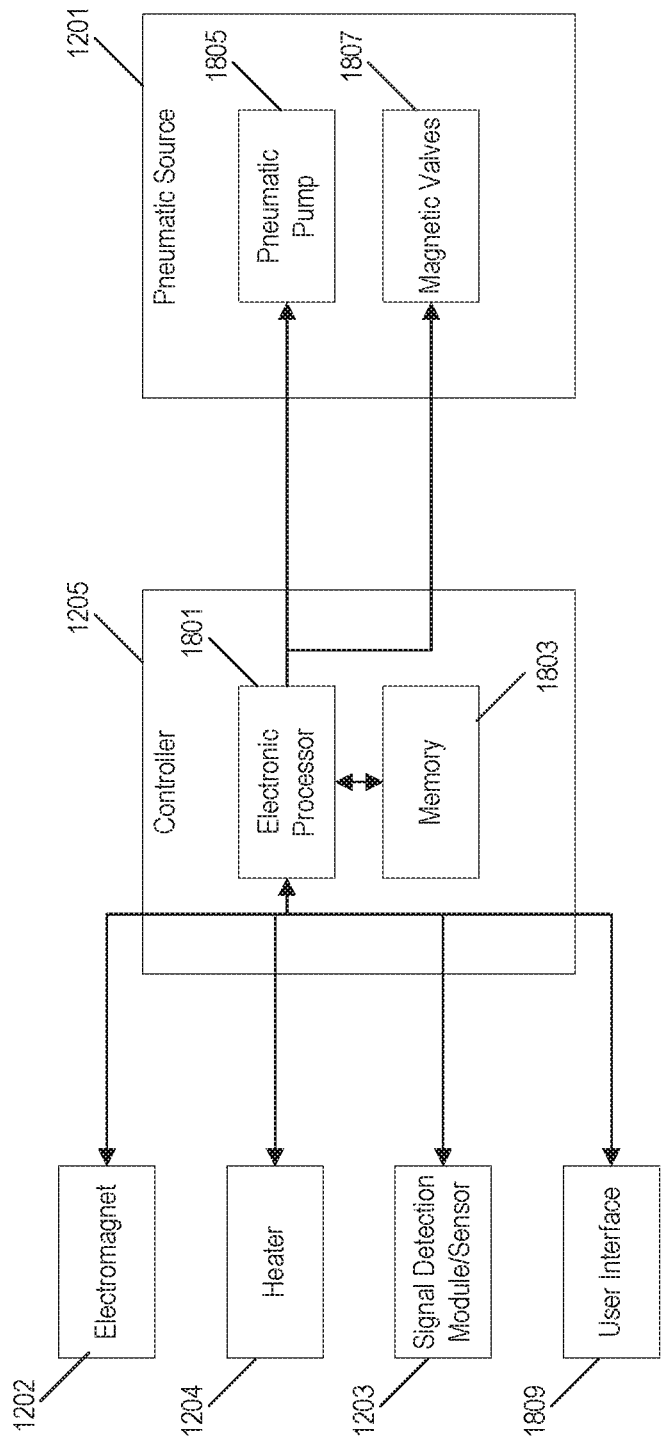
FIG. 18 is a block diagram of a control system of the system of FIG. 17.

As shown in FIG. 18, the pneumatic source 1201 includes one or more controllable pneumatic pumps 1805 and a series of magnetically actuated valves 1807. The electronic controller 1205 is configured to transmit control signals to the pneumatic pump(s) 1805 to cause the pneumatic pump(s) to turn on, turn off, and, in some implementations, to adjust/regulate the pneumatic pressure generated by the pneumatic pump(s). The electronic controller 1205 is also configured to transmit control signals to the magnetic valves to selectively control the opening and closing of the valves. In this example, the pneumatic source 1201 includes a magnetic valve 1807 corresponding to each connector port 215 of the cartridge 100 and, accordingly, by operating the magnetic valves 1807, the electronic controller 1205 is able to control when pneumatic pressure generated by the pneumatic pump (s) 1805 is applied to each individual connector port 215 of the cartridge 100. Similarly, the electronic controller 1205 in this example is configured to generate control signals to the heater 1204 to control the activation/deactivation of the heater 1204 and to generate control signals to the electromagnet 1202 to control the activation/deactivation of the electromagnet 1202.

Also, in some implementations (as illustrated in FIG. 18), the electronic controller 1205 is also communicatively coupled to a user interface 1809 (e.g., a display screen and a user input device such as a mouse, a keyboard, or a touch-sensitive display screen). In such implementations, the electronic controller 1205 may be configured to receive user control inputs from a user through the user interface 1809 and/or to display information relating to the fluid analysis being performed (e.g., status updates and/or instructions to the user) and the results of the analysis (e.g., based on the output from the signal detection module/sensor 1203).

Figure 19A:
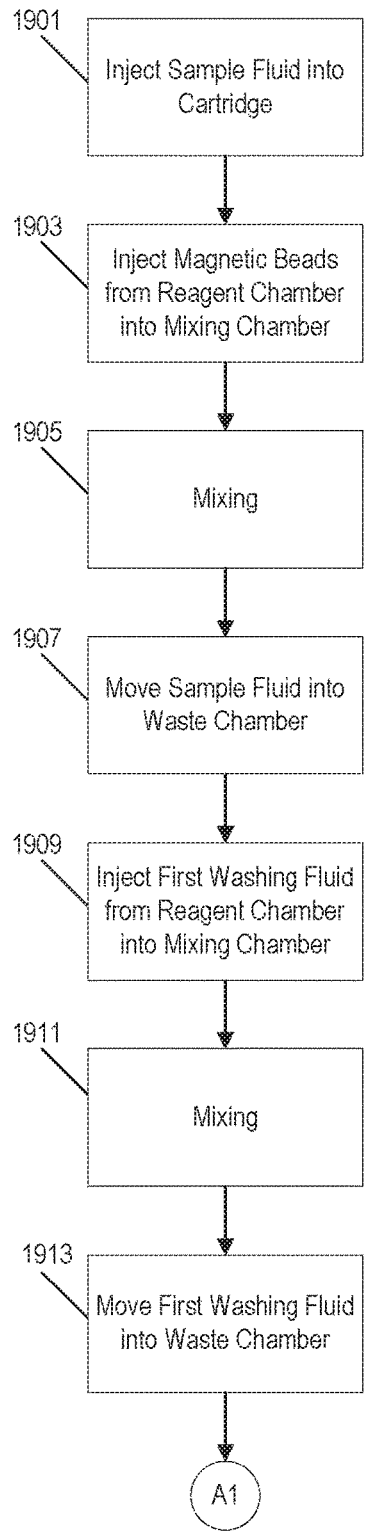
Figure 20A:
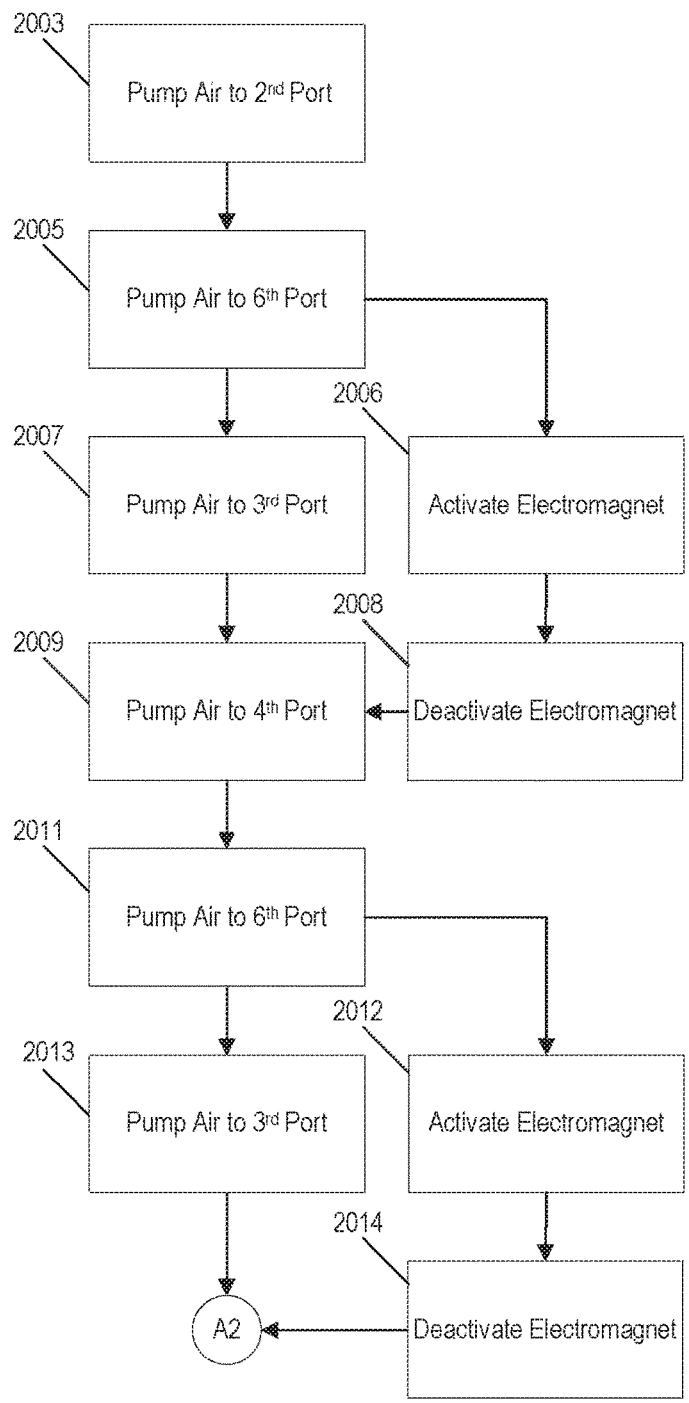
Figure 21A:
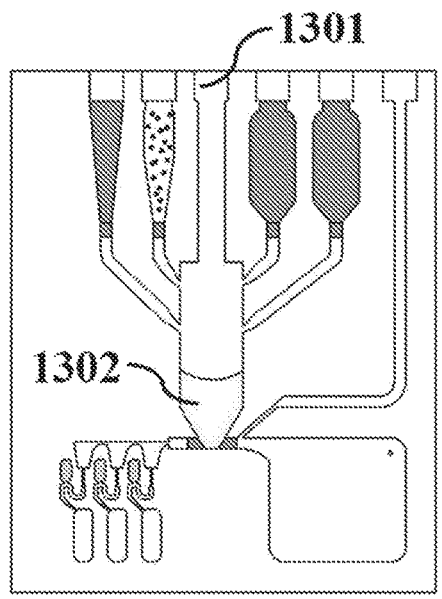
FIGS. 21A through 21O are partially transparent elevation views of the cartridge of FIG. 1 throughout the method of FIGS. 19A through 19C.
Figure 21B:
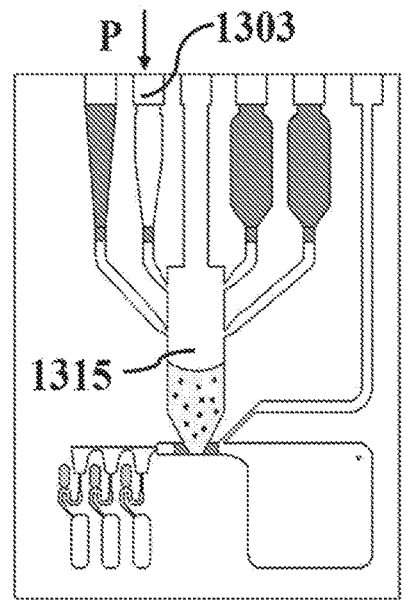
Figure 21C:
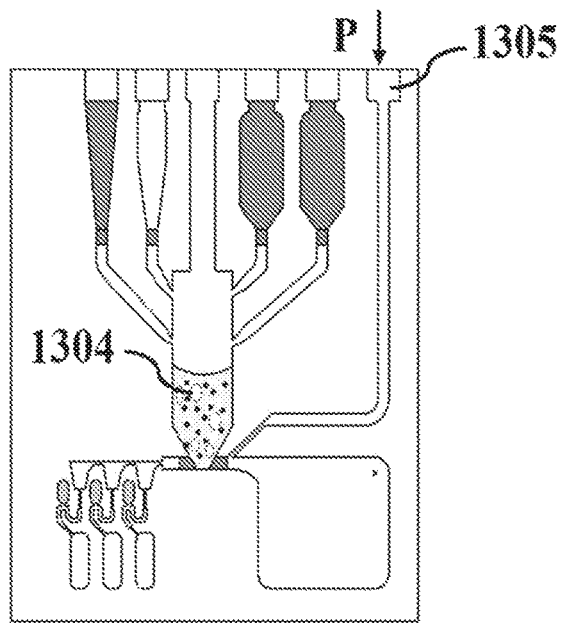
Figure 21D:
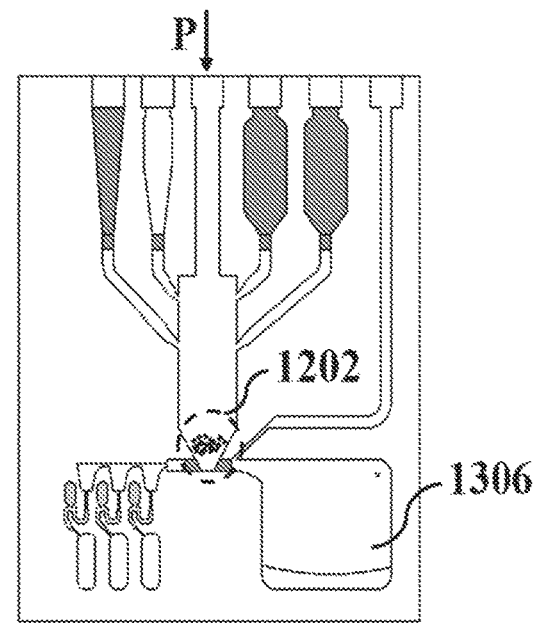
Figure 21E:
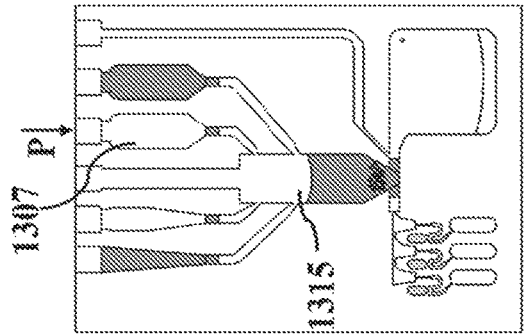
Figure 21F:
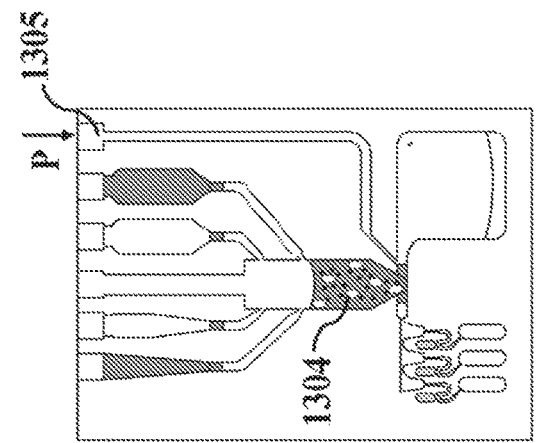
Figure 21G:
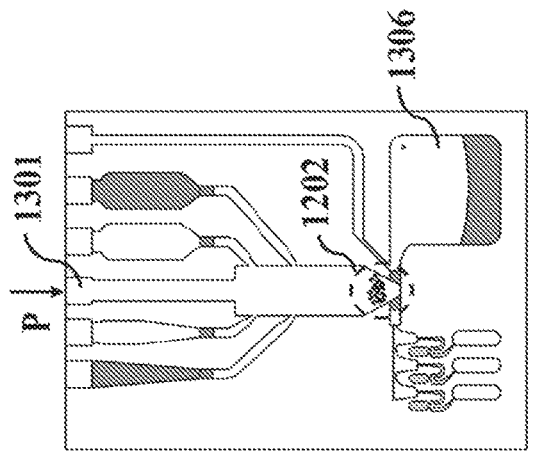
Figure 21H:
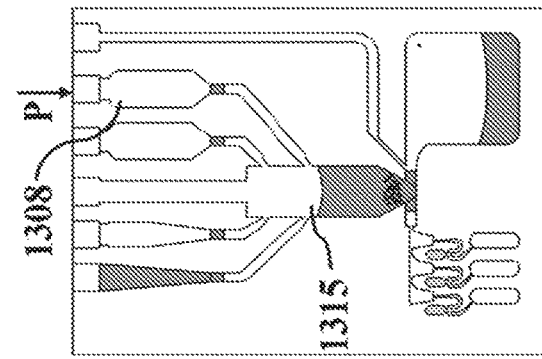
Figure 21I:
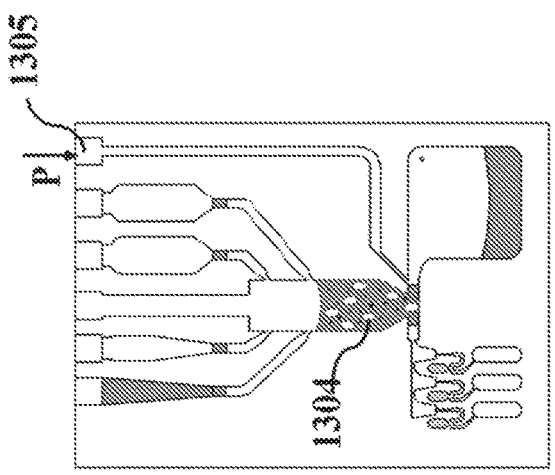
Figure 21J:
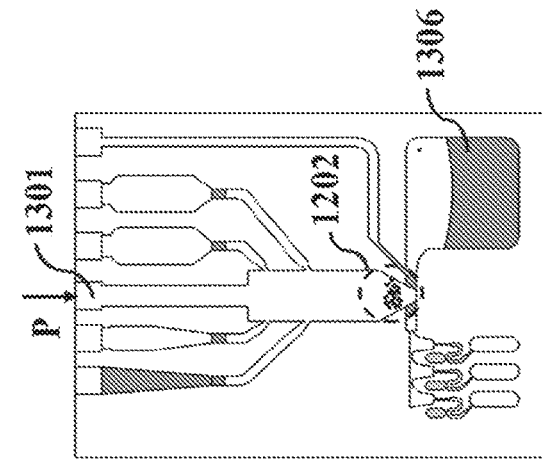
Figure 21L:
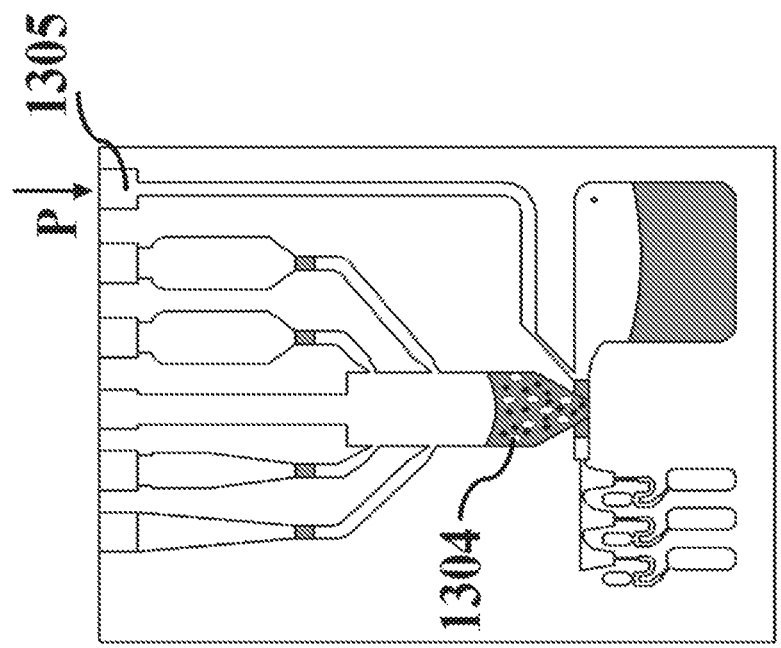
Figure 21K:
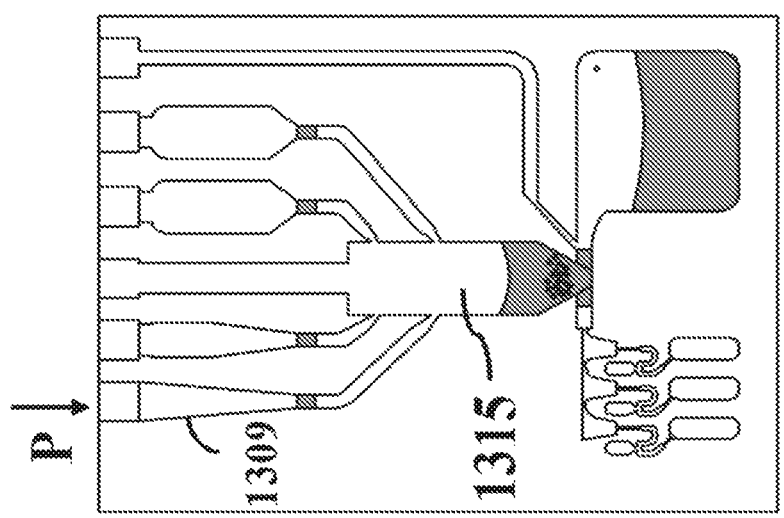
Figure 21M:
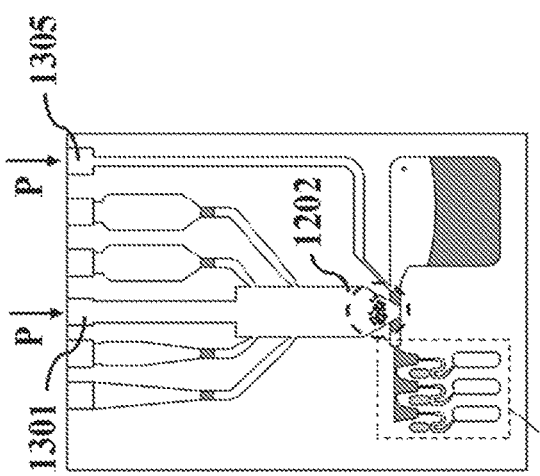
Figure 21N:
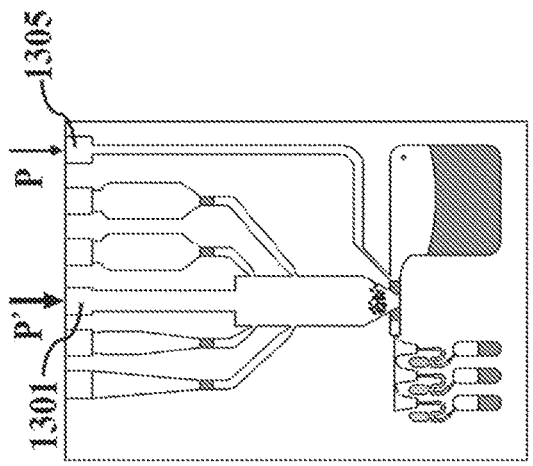
Figure 21O:
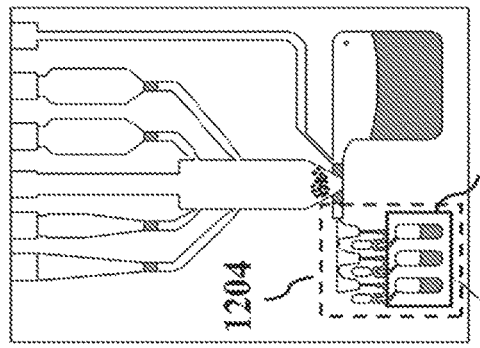
Figure 22A:
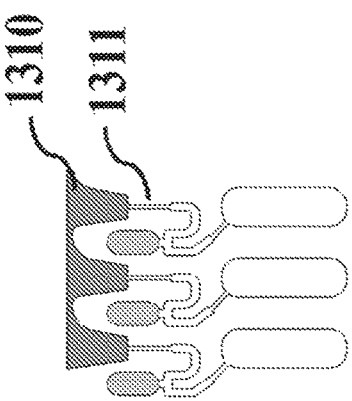
FIG. 22A is a detailed elevation view of the metering mechanism of the cartridge of FIG. 1 during the method of FIGS. 19A through 19C before sealing of the reacting chambers.
Figure 22B:
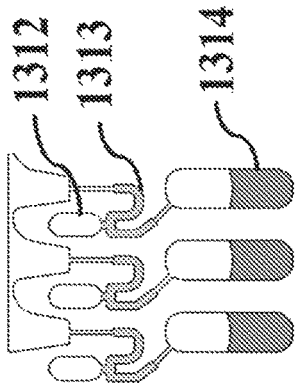
FIG. 22B is a detailed elevation view of the metering mechanism of the cartridge of FIG. 1 during the method of FIGS. 19A through 19C after sealing of the reacting chambers.

FIGS. 19A through 22B illustrate an example of a fluid analysis processes performed by the system of FIG. 17A. In particular, FIGS. 19A through 19C illustrate the actions performed by the cartridge 100, FIGS. 20A through 20C illustrate the actions performed by the electronic controller 1205 to cause the actions performed by the cartridge 100, FIGS. 21A through 21O graphically illustrate the movement of fluids within the cartridge 100 during each step of the method of FIGS. 19A through 19C; and FIGS. 22A and 22B illustrate the operation of the metering mechanism for the reacting chambers of the cartridge 100 in further detail.

First, as illustrated in the FIG. 21A, a fluid sample 1302 is injected into the mixing chamber 1301 of the cartridge 100 (step 1901, FIG. 19A). In this example, a 300 µL fluid sample 1302 is injected through the $3^{rd}$ Port of the connector structure 201. However, in other implementations, the system may be configured to automatically measure and dispense the fluid sample into the mixing chamber 1301 (e.g., through the $3^{rd}$ Port). Next, as illustrated in FIG. 21B, the electronic controller 1205 operates the pneumatic source 1201 to apply a pressure P to the $2^{nd}$ Port of the connector structure 201 (step 2003, FIG. 20A) causing magnetic beads 1315 in a 526 µL buffer fluid to move from the magnetic bead reagent chamber 1303 into the mixing chamber 1301 (step 1903, FIG. 19A).

As illustrated in FIG. 21C, air bubbles 1304 are then generated in the mixing chamber 1301 to mix the fluid sample 1302 and the magnetic beads 1315 (step 1905, FIG. 19A) which facilitates binding between the magnetic beads 1315 and a material of interest in the fluid sample 1302. This mixing is applied by the electronic controller 1205 operating the pneumatic source 1201 to apply a pressure P to the $6^{th}$ port of the connector structure 201 (step 2005, FIG. 20A) causing air to flow through the air flow channel 1305, which, in turn, inflates the elastic layer within the waste collection chamber 1306, opens the FAST valve/switch between the waste collection chamber 1306 and the mixing chamber 1301, and releases the pressurized air as air bubbles 1304 from the waste collection chamber 1306 into the mixing chamber 1301 below the fluid mixture within the mixing chamber 1301.

After mixing of the sample fluid and magnetic beads is completed, the electronic controller 1205 activates the electromagnet 1202 (step 2006, FIG. 20A) and applies the pressure P to the $3^{rd}$ Port of the connector structure 201 (step 2007, FIG. 20A). As illustrated in FIG. 21D, the pressure applied to the $3^{rd}$ Port opens the low pressure lever valve between the mixing chamber 1301 and the waste collection chamber 1306 causing the sample fluid to flow into the waste collection chamber 1306 (step 1907, FIG. 19A) while the activated electromagnet 1202 holds the magnetic beads 1315 (and the sample material coupled thereto) in the mixing chamber 1301. The electromagnet 1202 is then deactivated (step 2008, FIG. 20A).

A first washing is then applied to the magnetic beads by the electronic controller 1205 applying the pressure P to the 4th Port (step 2009, FIG. 20A), which, as illustrated in FIG. 21E causes a first washing fluid to flow from a first washing fluid reagent chamber 1307 into the mixing chamber 1301 where the magnetic beads 1315 remain (step 1909, FIG. 19A). Mixing is then applied to the first washing fluid and the magnetic beads (step 1911, FIG. 19A) by the electronic controller 1205 applying the pressure P to the 6th Port (step 2011, FIG. 20A), which generates air bubbles 1304 released at the bottom of the mixing chamber 1301 as described above and as illustrated in FIG. 21F. The first washing fluid is then moved from the mixing chamber 1301 into the waste collection chamber 1306 (step 1913, FIG. 19A) by the electronic controller 1205 activating the electromagnet 1202 (step 2012, FIG. 20A) and then applying the pressure P to the $3^{rd}$ Port (step 2013, FIG. 20A) as illustrated in FIG. 21G. After the first washing fluid is removed from the mixing chamber 1301, the electronic controller 1205 deactivates the electromagnet 1202 (step 2014, FIG. 20A).

Figure 19B:
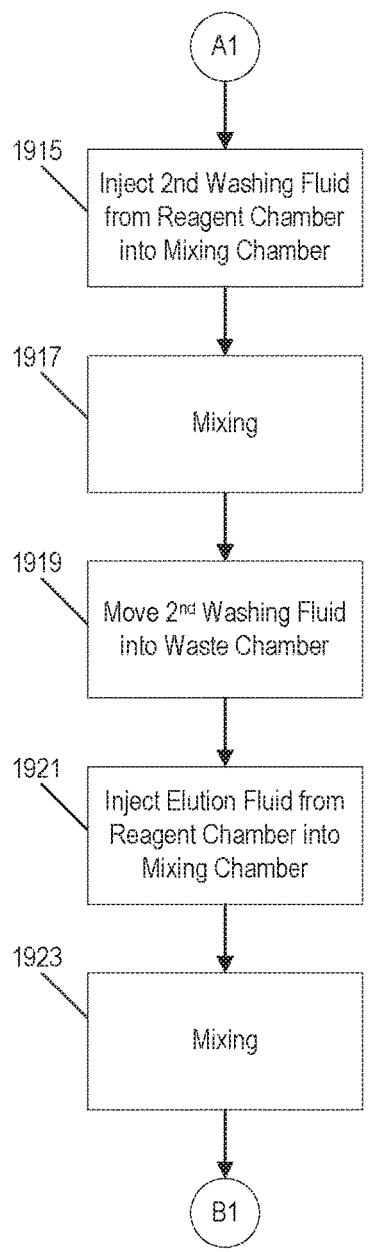
Figure 20B:
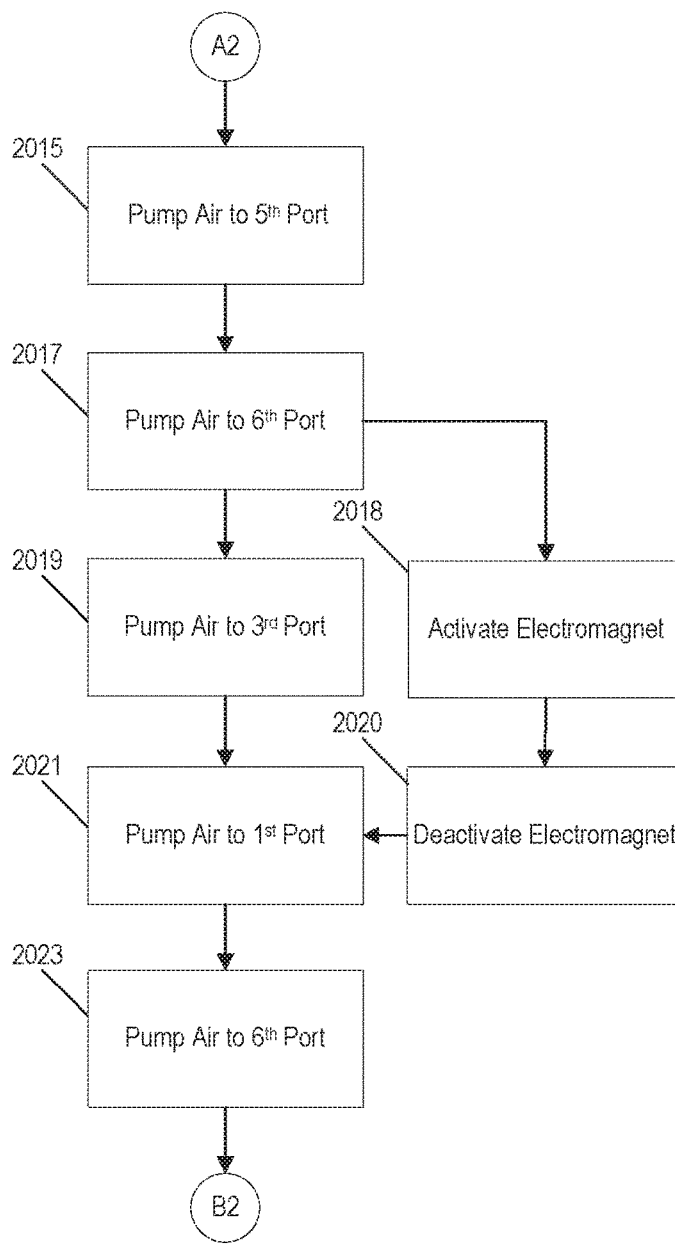

Similarly, a second washing is then applied to the magnetic beads by the electronic controller 1205 applying the pressure P to the $5^{th}$ Port (step 2015, FIG. 20B), which, as illustrated in FIG. 21H causes a second washing fluid to flow from a second washing fluid reagent chamber 1308 into the mixing chamber 1301 where the magnetic beads 1315 remain (step 1915, FIG. 19B). Mixing is then applied to the second washing fluid and the magnetic beads (step 1917, FIG. 19B) by the electronic controller 1205 applying the pressure P to the $6^{th}$ Port (step 2017, FIG. 20B), which generates air bubbles 1304 released at the bottom of the mixing chamber 1301 as described above and as illustrated in FIG. 21I. The second washing fluid is then moved from the mixing chamber 1301 into the waste collection chamber 1306 (step 1919, FIG. 19B) by the electronic controller 1205 activating the electromagnet 1202 (step 2018, FIG. 20B) and then applying the pressure P to the $3^{rd}$ Port (step 2019, FIG. 20B) as illustrated in FIG. 21J. After the second washing fluid is removed from the mixing chamber 1301, the electronic controller 1205 deactivates the electromagnet 1202 (step 2020, FIG. 20B).

With the material of interest from the sample bound to the magnetic beads 1315 and having performed washing of the magnetic beads 1315, the system now performs an elution process to release the material of interest from the magnetic beads 1315. The electronic controller 1205 applies the pressure P to the $1^{st}$ Port (step 2021, FIG. 20B), which causes an elution fluid to move from an elution reagent chamber 1309 into the mixing chamber 1301 where the magnetic beads 1315 remain (step 1921, FIG. 19B) as illustrated in FIG. 21K. Mixing is then applied to the elution fluid and the magnetic beads (step 1923, FIG. 19B) by the electronic controller 1205 applying the pressure P to the $6^{th}$ Port (step 2023, FIG. 20B), which generates air bubbles 1304 released at the bottom of the mixing chamber 1301 as described above and as illustrated in FIG. 21L.

Mixing the magnetic beads with the elution fluid causes the material of interest from the sample to be released from the magnetic beads and, after mixing, the material of interest from the sample is suspended in the elution fluid. To perform PCR testing on the material of interest, the elution fluid is now transported from the mixing chamber 1301 into the metering chamber 1310 (step 1925, FIG. 19C). This is performed by the electronic controller 1205 activating the electromagnet 1202 (step 2024, FIG. 20C) and then operating the pneumatic source 1201 to simultaneously apply the pressure P to both the $3^{rd}$ Port (step 2025, FIG. 20C) and the $6^{th}$ Port (step 2026, FIG. 20C). As illustrated in FIG. 21M, this combined pressure applied to the $3^{rd}$ Port and the $6^{th}$ Port causes the high pressure lever switch to open and causes the elution fluid (and the material of interest from the sample suspended therein) to flow into the metering chamber 1310 while the magnetic beads remain held by the electromagnet 1202 in the mixing chamber 1301. However, as illustrated in further detail in FIG. 22A, a relatively larger liquid resistance prevents the elution fluid from moving through the narrow channel 1311 into the reacting chambers 1314.

After the elution fluid is moved into the metering chamber 1310, the electronic controller 1205 increases the air pressure applied to the $3^{rd}$ Port from the initial control pressure P to a higher pressure P' (step 2027, FIG. 20C) while continuing to apply the pressure P to the $6^{th}$ Port (step 2028, FIG. 20C) and keeping the electromagnet 1202 active (step 2029, FIG. 20C). As illustrated in FIG. 21N, increasing the pressure applied to the $3^{rd}$ Port in this way increases the total internal pressure within the mixing chamber 1301 and, because the high pressure lever switch between the mixing chamber 1301 and the metering chamber 1310 remains open, this higher total internal pressure pushes the elution fluid past the respective narrow channels 1311 and into the reacting chambers 1314 (step 1927, FIG. 19C). The electronic controller 1205 deactivates the electromagnet 1202 after the elution fluid and the material of interest therein is moved into the reacting chambers 1214 (step 2030, FIG. 20C).

As illustrated in FIG. 22A (and as discussed above), the metering chamber 1310 is formed as a single chamber with three different sections. Because the liquid resistance provided by the narrow channels 1311 prevents the elution fluid from moving into the reacting chambers 1314, the elution fluid fills all three sections of the metering chamber 1310 before moving on to the reacting chambers 1314. Furthermore, each the metering chamber 1310 is designed so that fluid in each section of the metering chamber 1310 can only flow into one corresponding reacting chamber 1314 (i.e., three reacting chambers 1314 corresponding to three sections of the metering chamber 1310). In this way, the relative size of the different sections of the metering chamber 1310 can be designed to control the amount of fluid that will be moved into each reacting chamber 1314.

After the elution fluid and the material of interest therein is moved into the reaction chambers 1314 and the electromagnet is deactivated, the system seals the reacting chambers (step 1931, FIG. 19C) by the electronic controller 1205 activating the heater 1204 (step 2031, FIG. 20C). As illustrated in FIG. 21O and as shown in further detail in FIG. 22B, activation of the heater 1204 causes a sealing material stored within the sealing material chambers 1313 to melt and flow into a sealing channel 1313. In this example, the sealing material is a paraffin wax and the heater 1204 is operated to heat the paraffin wax to a temperature of 50° C. At this temperature, the paraffin wax melts and flows into the sealing channel 1313. The temperature of the heater 1204 is then further increased to a temperature of around 100° C. to heat the materials within the reacting chambers 1314 during the reaction (step 2032, FIG. 20C). At the elevated temperature, the sealing material remains in the liquid state within the sealing channel 1313, but it does not react with the PCR reagents and also serves as a "liquid plug" to prevent the vapor from exiting the reacting chambers 1314 (e.g., in case of chemical contamination). After the reacting chambers 1314 are sealed the electronic controller 1205 operates the sample analysis module/sensor 1203 (step 2033, FIG. 20C) to perform the sample analysis on the material sealed in the reacting chambers 1314 (step 1933, FIG. 19C).

The systems and methods described in the examples above are only a few specific examples of implementations. Other implementations and variations are possible. Additionally, the examples described above and the accompanying claims may use phrases such as "a first pressure," "a second pressure," etc. to separately refer to pressures applied to specific parts of the system at different times. These different phrases do not necessarily imply different pressure magnitudes. Accordingly, unless explicitly stated otherwise, a 'first pressure" could be applied with the same pressure magnitude as a "second pressure." Various features and advantages of the invention are set forth by the following claims.

What is claimed is:

1. A pneumatic-driven fluidic cartridge comprising:
a substrate layer, wherein a fluid channel formed in a surface of the substrate layer includes a first chamber and a second chamber separated by a block section,
an actuator layer including a lever formed in the actuator layer and extending from the second chamber across the block section to the first chamber; and
an elastic layer positioned between the substrate layer and the actuator layer,
wherein the lever of the actuator layer applies a sealing force to the elastic layer at the block section sufficient to prevent fluid flow from the first chamber to the second chamber when a pressure acting on the elastic layer from within the fluid channel is less than a first threshold pressure,
wherein the lever is configured to become bent outwardly by the pressure acting on the elastic layer from within the fluid channel in response to the pressure acting on the elastic layer from within the fluid channel exceeding the first threshold pressure, and
wherein the outward bending of the lever is configured to allow fluid to flow from the first chamber to the second chamber between the block section and the elastic layer.

2. The pneumatic-driven fluidic cartridge of claim 1, further comprising an adhesive layer positioned between the substrate layer and the elastic layer, wherein the adhesive layer adheres the elastic layer to the substrate layer to seal the fluid channel without adhering the block section of the substrate layer to the elastic layer.

3. The pneumatic-driven fluidic cartridge of claim 1, wherein the substrate layer further includes a third chamber separated from the second chamber by a second block section,
wherein the lever of the actuator layer further extends from the third chamber across the second block section across the second chamber across the block section to the first chamber,
wherein the sealing force applied by the lever of the actuator layer to the elastic layer is further sufficient to prevent fluid flow from the second chamber to the third chamber when the pressure acting on the elastic layer from within the fluid channel is less than the first threshold pressure, and
wherein the outward bending of the lever is configured to further allow fluid to flow from the second chamber to the third chamber between the second block section and the elastic layer.

4. The pneumatic-driven fluidic cartridge of claim 1, wherein the substrate layer further includes a third chamber separated from the first chamber by a second block section,
wherein the lever formed in the actuator layer is a first lever, wherein the actuator layer further includes a second lever formed in the actuator layer and extending from the third chamber across the second block section to the first chamber,
wherein the second lever is configured to become bent outwardly by the pressure acting on the elastic layer from within the fluid channel in response to the pressure acting on the elastic layer from within the fluid channel exceeding a second threshold pressure, and
wherein the outward bending of the second lever is configured to allow fluid to flow from the first chamber to the third chamber between the second block section and the elastic layer.

5. The pneumatic-driven fluid cartridge of claim 4, wherein a length of the first lever is greater than a length of the second lever, wherein the length of the second lever affects the second threshold pressure such that the first lever is configured to become displaced by lower pressures than the second lever.

6. A pneumatic-driven fluid cartridge system, comprising an electronic controller, a pneumatic pump, and the pneumatic-driven fluid cartridge of claim 5,
wherein the electronic controller is configured to cause fluid to flow from the first chamber to the second chamber by operating the pneumatic pump to apply a first pneumatic pressure to the first chamber, wherein the first pneumatic pressure is greater than the first pressure threshold and less than the second pressure threshold, and
wherein the electronic controller is configured to cause fluid to flow from the first chamber to the third chamber by operating the pneumatic pump to apply a second pneumatic pressure to the first chamber, wherein the second pneumatic pressure is greater than the second pressure threshold.

7. The pneumatic-driven fluid cartridge system of claim 6, wherein the first chamber includes a branched chamber including a first sub-chamber positioned adjacent to the first block and a second sub-chamber positioned adjacent to the second block, wherein the first chamber is configured such that fluid in the second sub-chamber does not flow into the first sub-chamber and does not flow from the first chamber into the third chamber when the second pneumatic pressure is applied by the pneumatic pump, and wherein the first chamber is configured such that fluid in the first sub-chamber does not flow into the second sub-chamber and does not flow from the first chamber into the second chamber when the first pneumatic pressure is applied by the pneumatic pump.

8. The pneumatic-driven fluid cartridge system of claim 6, wherein the substrate layer further includes a second pneumatic channel extending from the controllable pneumatic pump to the second chamber, wherein the electronic controller is configured to apply the second pneumatic pressure to the first chamber by operating the pneumatic pump to apply a third pneumatic pressure to the second chamber through the second pneumatic channel while applying the first pneumatic pressure to the first chamber, wherein the second pneumatic pressure includes a combination of the first pneumatic pressure applied to the first chamber and the third pneumatic pressure passing from the second chamber into the first chamber between the block area and the elastic layer.

9. The pneumatic-driven fluid cartridge system of claim 8, wherein the electronic controller is configured to provide a pneumatic mixing force to fluid in the first chamber by operating the pneumatic pump to apply a fourth pneumatic pressure to the second chamber through the second pneumatic channel causing bubbles to enter the first chamber below the fluid in the first chamber, wherein the fourth pneumatic pressure is greater than the first pressure threshold and less than the second pressure threshold.

10. The pneumatic-driven fluid cartridge system of claim 9, wherein the substrate layer further includes a fourth chamber separated from the first chamber by a third block section, wherein the electronic controller is further configured to cause a sample fluid to flow from the fourth chamber into the first chamber by operating the pneumatic pump to apply a fifth pneumatic pressure to the fourth chamber.

11. The pneumatic-driven fluid cartridge system of claim 9, further comprising an electromagnet positioned adjacent to the first chamber and operated by the electronic controller to selectively apply a magnetic field to the first chamber, wherein the electronic controller is configured to:
   apply the pneumatic mixing force to the first chamber, wherein the pneumatic mixing force causes a sample fluid to mix with a plurality of magnetic beads in the first chamber,
   apply the first pneumatic pressure to the first chamber after applying the pneumatic mixing force, wherein applying the first pneumatic pressure causes the sample fluid to flow from the first chamber into the second chamber, and
   activate the electromagnet while applying the first pneumatic pressure to the first chamber to prevent the magnetic beads from flowing from the first chamber into the second chamber with the sample fluid.

12. The pneumatic-driven fluid cartridge system of claim 11, wherein the substrate layer further includes a fifth chamber separated from the first chamber by a fourth block section, wherein the electronic controller is further configured to:
   deactivate the electromagnet and remove the first pneumatic pressure from the first chamber,
   cause a first washing fluid to flow from the fifth chamber into the first chamber by applying a sixth pneumatic pressure to the fifth chamber,
   apply the pneumatic mixing force to the first chamber after causing the first washing fluid to flow from the fifth chamber into the first chamber,
   apply the first pneumatic pressure to the first chamber after applying the pneumatic mixing force, wherein applying the first pneumatic pressure causes the first washing fluid to flow from the first chamber into the second chamber, and
   activate the electromagnet while applying the first pneumatic pressure to the first chamber to prevent the magnetic beads from flowing from the first chamber into the second chamber with the first washing fluid.

13. The pneumatic-driven fluid cartridge system of claim 12, wherein the substrate layer further includes a sixth chamber separated from the first chamber by a fifth block section, wherein the electronic controller is further configured to:
   deactivate the electromagnet and remove the first pneumatic pressure from the first chamber,
   cause a second washing fluid to flow from the sixth chamber into the first chamber by applying a seventh pneumatic pressure to the sixth chamber,
   apply the pneumatic mixing force to the first chamber after causing the second washing fluid to flow from the fifth chamber into the first chamber,
   apply the first pneumatic pressure to the first chamber after applying the pneumatic mixing force, wherein applying the first pneumatic pressure causes the second washing fluid to flow from the first chamber into the second chamber, and
   activate the electromagnet while applying the first pneumatic pressure to the first chamber to prevent the magnetic beads from flowing from the first chamber into the second chamber with the second washing fluid.

14. The pneumatic-driven fluid cartridge system of claim 12, wherein the substrate layer further includes a seventh chamber separated from the first chamber by a sixth block section, wherein the electronic controller is further configured to:
   cause an elution fluid to flow from the seventh chamber into the first chamber by applying an eighth pneumatic pressure to the seventh chamber, wherein the elution fluid is configured to release sample from the magnetic beads,
   apply the pneumatic mixing force to the first chamber after causing the elution fluid to flow from the seventh chamber into the first chamber,
   apply the second pneumatic pressure to the first chamber and the third pneumatic pressure to the second chamber after applying the pneumatic mixing force, wherein applying the second pneumatic pressure to the first chamber and the third pneumatic pressure to the second chamber causes the elution fluid and the eluted sample to flow from the first chamber into the third chamber, and
   activate the electromagnet while applying the second pneumatic pressure to the first chamber and the third pneumatic pressure to the second chamber to prevent the magnetic beads from flowing from the first chamber into the third chamber with the elution fluid and the eluted sample.

15. The pneumatic-driven fluid cartridge system of claim 6, wherein the third chamber is a metering chamber, wherein the substrate layer further includes a plurality of reacting chambers each separated from the metering chamber by a different one of a plurality of narrow channels, wherein the electronic controller is further configured to:
 operate the pneumatic pump to apply a ninth pneumatic pressure to the metering chamber through the first chamber, wherein the ninth pneumatic pressure is greater than the second pneumatic pressure and causes fluid in the metering chamber to flow through the narrow channels into the reacting chambers.

16. The pneumatic-driven fluid cartridge system of claim 15, wherein the substrate layer further includes one or more sealing material chambers coupled to the plurality of narrow channels, the system further comprising a selectively activatable heater positioned proximate to the one or more sealing material chambers, wherein the electronic controller is further configured to seal the reacting chambers after causing the fluid in the metering chamber to flow into the reacting chambers by operating the selectively activatable heater to cause a sealing material in the one or more sealing material chambers to melt and flow into the narrow channels.

17. The pneumatic-driven fluid cartridge system of claim 15, further comprising a signal detection sensor coupled to each of the plurality of reacting chambers, wherein the signal detection sensor is configured to output a signal indicating of at least one characteristic of the sample in the plurality of reacting chambers.

18. A cartridge device for fluid sample analysis, the cartridge device comprising:
 a substrate layer including, formed into a first surface of the substrate layer, a plurality of reagent chambers, a mixing chamber, a waste collection chamber, and at least one reacting chamber,
  wherein the substrate layer includes a plurality of block areas separating each reagent chamber from the mixing chamber, separating the mixing chamber from the waste collection chamber, and separating the mixing chamber from the at least one reacting chamber;
 an elastic layer adhesively coupled to the first surface of the substrate layer, wherein the elastic layer is not adhesively coupled to the substrate layer at the block areas;
 an actuator layer separated from the substrate layer by the elastic layer, wherein the actuator layer includes
  a plurality of displaceable reagent levers formed in the actuator layer and each positioned to extend across a different one of the block areas separating a reagent chamber from the mixing chamber, wherein each lever of the plurality of displaceable reagent levers is configured to
   restrict fluid flow from a different one of the plurality of reagent chambers into the mixing chamber by applying a force to the elastic layer at the block area separating the reagent chamber from the mixing chamber, and
   bend outwardly away from the substrate layer in response to a sufficient pneumatic pressure applied to the reagent chamber, wherein the outward bending of the lever allows fluid to flow from the reagent chamber into the mixing chamber,
  a waste collection chamber lever formed in the actuator layer and positioned to extend across the block area separating the mixing chamber from the waste collection chamber, wherein the waste collection chamber lever is configured to restrict fluid flow from the mixing chamber into the waste collection chamber by applying a second force to the elastic layer above the block area separating the mixing chamber from the waste collection chamber and to bend outwardly away from the substrate layer in response to a first pneumatic pressure applied to the mixing chamber, wherein the outward bending of the waste collection chamber lever allows fluid to flow from the mixing chamber into the waste collection chamber, and
  a reacting chamber lever formed in the actuator layer and positioned to extend across the block area separating the mixing chamber from the at least one reacting chamber, wherein the reacting chamber lever is configured to restrict fluid flow from the mixing chamber into the at least one reacting chamber by applying a third force to the elastic layer above the block area separating the mixing chamber from the at least one reacting chamber and to bend outwardly away from the substrate layer in response to a second pneumatic pressure applied to the mixing chamber, wherein the outward bending of the reacting chamber lever allows fluid to flow from the mixing chamber to the at least one reacting chamber,
  wherein the waste collection chamber lever is configured to outwardly bend in response to lower pneumatic pressure in the mixing chamber than the second pneumatic pressure required to outwardly bend the reacting chamber lever; and
 a connector coupled to a top edge of the cartridge, wherein the connector includes a plurality of openings each couplable to a pneumatic pump, wherein the plurality of openings includes:
  a mixing chamber opening coupled to the mixing chamber, and
  a plurality of reagent chamber openings each coupled to a different one of the plurality of reagent chambers.

19. The cartridge device of claim 18, wherein the substrate layer further includes a pneumatic mixing channel formed into the first surface of the substrate layer, wherein the pneumatic mixing channel extends from the top edge of the substrate layer to the waste collection chamber, wherein the plurality of openings of the connector further includes a pneumatic mixing opening coupled to the pneumatic mixing channel, wherein a pneumatic mixing pressure applied to the pneumatic mixing channel causes the outward bending of the waste collection chamber lever and creates bubbles in a fluid in the mixing chamber.

20. A method of performing fluid sample analysis using the cartridge device of claim 18, the method comprising:
 adding a fluid sample into the mixing chamber through the mixing chamber opening of the connector;
 add a plurality of magnetic beads into the mixing chamber by applying a pneumatic pressure to a first reagent chamber opening of the connector to cause the plurality magnetic beads to flow from a first reagent chamber of the plurality of reagent chambers into the mixing chamber, wherein the magnetic beads are configured to bind to a material of interest in the fluid sample;
 drain the fluid sample from the mixing chamber by applying a first pneumatic pressure to the mixing chamber through the mixing chamber opening of the connector while activating an electromagnet positioned proximate to the mixing chamber to cause the fluid sample to flow from the mixing chamber into the waste collection chamber and prevent the magnetic beads from flowing into the waste collection chamber;

washing the magnetic beads by applying the pneumatic pressure to a second reagent chamber opening of the connector to cause a washing fluid to flow from the second reagent chamber of the plurality of reagent chambers into the mixing chamber;

draining the washing fluid from the mixing chamber by applying a first pneumatic pressure to the mixing chamber through the mixing chamber opening of the connector while activating the electromagnet to cause the fluid sample to flow from the mixing chamber into the waste collection chamber and prevent the magnetic beads from flowing into the waste collection chamber;

eluting the material of interest from the magnetic beads by applying the pneumatic pressure to a third reagent chamber opening of the connector to cause an eluting fluid to flow from the third reagent chamber of the plurality of reagent chambers into the mixing chamber; and advancing the eluted material of interest into the one or more reacting chambers by applying the second pneumatic pressure to the mixing chamber through the mixing chamber opening of the connector while activating the electromagnet to cause the eluted material of interest to flow from the mixing chamber into the one or more reacting chambers and prevent the magnetic beads from flowing into the one or more reacting chambers.

* * * * *